(12) United States Patent
Mortarino et al.

(10) Patent No.: US 9,308,070 B2
(45) Date of Patent: Apr. 12, 2016

(54) PLIABLE SILK MEDICAL DEVICE

(71) Applicant: Allergan, Inc., Irvine, CA (US)

(72) Inventors: Enrico Mortarino, Hickory, NC (US); Jessica L. Akers, Cambridge, MA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/462,473

(22) Filed: Aug. 18, 2014

(65) Prior Publication Data

US 2015/0148823 A1 May 28, 2015

Related U.S. Application Data

(63) Continuation-in-part of application No. 13/715,872, filed on Dec. 14, 2012, which is a continuation-in-part of application No. 13/306,325, filed on Nov. 29, 2011, which is a continuation-in-part of application No. 13/186,151, filed on Jul. 19, 2011, which is a continuation-in-part of application No. 13/156,283, filed on Jun. 8, 2011, now abandoned, which is a continuation-in-part of application No. 12/680,404, filed as application No. PCT/US2009/063717 on Nov. 9, 2009, now abandoned.

(60) Provisional application No. 61/122,520, filed on Dec. 15, 2008.

(51) Int. Cl.
| | |
|---|---|
| *D04B 21/12* | (2006.01) |
| *A61F 2/00* | (2006.01) |
| *A61F 2/12* | (2006.01) |
| *A61L 31/00* | (2006.01) |
| *A61L 31/14* | (2006.01) |
| *A61L 27/36* | (2006.01) |

(52) U.S. Cl.
CPC ............... *A61F 2/0063* (2013.01); *A61F 2/12* (2013.01); *A61L 27/3604* (2013.01); *A61L 31/005* (2013.01); *A61L 31/148* (2013.01); *D04B 21/12* (2013.01); *A61F 2002/0068* (2013.01); *A61F 2210/0004* (2013.01); *D10B 2211/04* (2013.01); *D10B 2509/08* (2013.01)

(58) Field of Classification Search
CPC ........ D04B 21/06; D04B 21/08; D04B 21/10; D04B 21/12
See application file for complete search history.

(56) References Cited

U.S. PATENT DOCUMENTS

| | | | |
|---|---|---|---|
| 848,605 A | * | 3/1907 | Schmid .............................. 8/138 |
| 1,300,696 A | | 4/1919 | Branson |

(Continued)

FOREIGN PATENT DOCUMENTS

| | | |
|---|---|---|
| CA | 2153150 A | 8/1994 |
| DE | 3917174 | 12/1990 |

(Continued)

OTHER PUBLICATIONS

Ajisawa, Akiyoshi, Dissolution of Silk Fibroin With Calciumchloride/Ethanol Aqueous Solution, J. Seric. Sci. Japan, 1998, 91-94, 67(2).

(Continued)

*Primary Examiner* — Danny Worrell
(74) *Attorney, Agent, or Firm* — Linda Allyson Nassif

(57) ABSTRACT

An implantable, pliable knitted silk mesh for use in human soft tissue support and repair having a particular knit pattern that substantially prevents unraveling and preserves the stability of the mesh when cut, the knitted mesh including at least two yarns laid in a knit direction and engaging each other to define a plurality of nodes.

12 Claims, 18 Drawing Sheets

(56) References Cited

U.S. PATENT DOCUMENTS

| | | | |
|---|---|---|---|
| 955,541 A | 4/1920 | Petersen | |
| 1,709,662 A * | 4/1929 | Holland | 8/138 |
| 1,815,279 A * | 7/1931 | Takamine | 8/138 |
| 1,828,736 A * | 10/1931 | Harvey, Jr. | 8/138 |
| 1,896,494 A * | 2/1933 | Myers et al. | 8/138 |
| 1,921,022 A * | 8/1933 | Burton | 178/63 R |
| 1,927,022 A | 9/1933 | Bueno | |
| 1,990,588 A * | 2/1935 | Rossner et al. | 106/151.1 |
| 2,040,949 A * | 5/1936 | Henry et al. | 8/138 |
| 3,124,136 A * | 3/1964 | Usher | 606/213 |
| 3,314,123 A | 4/1967 | Groebli | |
| 3,552,154 A | 1/1971 | Lesley | |
| 3,595,276 A * | 7/1971 | Wrzesien | 139/11 |
| 3,672,187 A | 6/1972 | Simpson | |
| 3,922,888 A | 12/1975 | Patterson | |
| 3,931,721 A * | 1/1976 | Adamson | 66/195 |
| 3,952,555 A | 4/1976 | Lesley | |
| 3,999,407 A | 12/1976 | Odham | |
| 4,089,071 A * | 5/1978 | Kalnberz et al. | 623/23.61 |
| 4,118,842 A * | 10/1978 | Norris et al. | 28/218 |
| 4,141,207 A * | 2/1979 | Mizushima et al. | 57/243 |
| 4,248,064 A | 2/1981 | Odham | |
| 4,282,954 A | 8/1981 | Hill | |
| 4,340,091 A * | 7/1982 | Skelton et al. | 139/383 R |
| 4,347,847 A | 9/1982 | Usher | |
| 4,388,364 A | 6/1983 | Sanders | |
| 4,461,298 A | 7/1984 | Shalaby et al. | |
| 4,518,640 A | 5/1985 | Wilkens | |
| 4,530,113 A | 7/1985 | Matterson | |
| 4,605,691 A | 8/1986 | Balazs et al. | |
| 4,631,188 A | 12/1986 | Stoy et al. | |
| 4,792,336 A * | 12/1988 | Hlavacek et al. | 623/13.18 |
| 4,816,028 A * | 3/1989 | Kapadia et al. | 623/1.52 |
| 4,865,031 A | 9/1989 | O'Keeffe | |
| 4,942,875 A | 7/1990 | Hlavacek et al. | |
| 4,981,487 A | 1/1991 | da Costa | |
| 4,984,570 A * | 1/1991 | Langen et al. | 602/44 |
| 4,987,665 A * | 1/1991 | Dumican et al. | 28/218 |
| 5,120,829 A * | 6/1992 | Pierschbacher et al. | 530/326 |
| 5,134,006 A * | 7/1992 | Irvin | 428/68 |
| 5,171,505 A * | 12/1992 | Lock | 264/202 |
| 5,178,630 A * | 1/1993 | Schmitt | 623/1.52 |
| 5,191,777 A | 3/1993 | Schnegg | |
| 5,245,012 A | 9/1993 | Lombari et al. | |
| 5,250,077 A * | 10/1993 | Fuse et al. | 8/128.1 |
| 5,252,285 A * | 10/1993 | Lock | 264/202 |
| 5,353,486 A * | 10/1994 | Schmidt et al. | 28/167 |
| 5,366,504 A * | 11/1994 | Andersen et al. | 623/1.5 |
| 5,385,836 A * | 1/1995 | Kimura et al. | 435/177 |
| 5,456,697 A * | 10/1995 | Chesterfield et al. | 606/228 |
| 5,456,711 A * | 10/1995 | Hudson | 623/1.5 |
| 5,490,602 A | 2/1996 | Wilson et al. | |
| 5,501,856 A | 3/1996 | Ohtori et al. | |
| 5,509,931 A * | 4/1996 | Schmitt | 623/1.52 |
| 5,569,273 A * | 10/1996 | Titone et al. | 606/151 |
| 5,584,884 A | 12/1996 | Pignataro | |
| 5,587,456 A | 12/1996 | Pierschbacher et al. | |
| 5,591,822 A | 1/1997 | Pierschbacher et al. | |
| 5,598,615 A * | 2/1997 | Takada | 28/159 |
| 5,606,019 A * | 2/1997 | Cappello | 530/329 |
| 5,631,011 A | 5/1997 | Wadstrom | |
| 5,643,043 A | 7/1997 | Pflum | |
| 5,674,276 A | 10/1997 | Andersen | |
| 5,700,559 A | 12/1997 | Sheu et al. | |
| 5,716,404 A | 2/1998 | Vacanti | |
| 5,728,810 A | 3/1998 | Lewis et al. | |
| 5,736,399 A | 4/1998 | Takezawa et al. | |
| 5,741,332 A | 4/1998 | Schmitt | |
| 5,760,176 A | 6/1998 | Pierschbacher et al. | |
| 5,771,716 A * | 6/1998 | Schlussel | 66/195 |
| 5,795,835 A | 8/1998 | Bruner et al. | |
| 5,849,040 A * | 12/1998 | Kanehisa | 8/401 |
| 5,919,232 A * | 7/1999 | Chaffringeon et al. | 424/423 |
| 5,951,506 A * | 9/1999 | Tsubouchi | 602/48 |
| 5,965,125 A | 10/1999 | Mineau-Hanschke | |
| 5,969,106 A | 10/1999 | Rothstein et al. | |
| 5,990,378 A * | 11/1999 | Ellis | 623/11.11 |
| 5,994,099 A | 11/1999 | Lewis et al. | |
| 6,004,888 A | 12/1999 | Sugimoto et al. | |
| 6,006,552 A | 12/1999 | Matsuda et al. | |
| 6,042,592 A * | 3/2000 | Schmitt | 606/151 |
| 6,074,722 A | 6/2000 | Cuccias | |
| 6,076,448 A | 6/2000 | Rexroad | |
| 6,080,689 A | 6/2000 | Kanehisa | |
| 6,090,116 A * | 7/2000 | D'Aversa et al. | 606/151 |
| 6,110,590 A * | 8/2000 | Zarkoob et al. | 428/364 |
| 6,113,623 A * | 9/2000 | Sgro | 606/215 |
| 6,129,761 A | 10/2000 | Hubbell | |
| 6,136,022 A * | 10/2000 | Nunez et al. | 623/1.1 |
| 6,146,418 A * | 11/2000 | Berman | 623/8 |
| 6,159,877 A * | 12/2000 | Scholz et al. | 442/103 |
| 6,164,339 A * | 12/2000 | Greenhalgh | 139/1 R |
| 6,169,074 B1 | 1/2001 | Montal et al. | |
| 6,171,984 B1 | 1/2001 | Paulson et al. | |
| 6,175,053 B1 | 1/2001 | Tsubouchi | |
| 6,175,533 B1 * | 1/2001 | Lee et al. | 365/230.05 |
| 6,228,132 B1 * | 5/2001 | Prince et al. | 8/594 |
| 6,233,978 B1 | 5/2001 | Gehring, Jr. et al. | |
| 6,258,124 B1 | 7/2001 | Darois et al. | |
| 6,270,530 B1 | 8/2001 | Eldridge et al. | |
| 6,287,316 B1 * | 9/2001 | Agarwal et al. | 606/151 |
| 6,287,340 B1 * | 9/2001 | Altman et al. | 623/13.11 |
| 6,302,922 B1 | 10/2001 | Kanehisa | |
| 6,303,136 B1 * | 10/2001 | Li et al. | 424/424 |
| 6,389,851 B1 | 5/2002 | Groshens | |
| 6,408,656 B1 * | 6/2002 | Ory et al. | 66/195 |
| 6,427,933 B1 | 8/2002 | Tsubouchi | |
| 6,440,740 B1 * | 8/2002 | Tsubouchi et al. | 435/402 |
| 6,443,964 B1 * | 9/2002 | Ory et al. | 606/151 |
| 6,506,394 B1 | 1/2003 | Yahiaoui et al. | |
| 6,530,956 B1 | 3/2003 | Mansmann | |
| 6,540,773 B2 * | 4/2003 | Dong | 623/1.13 |
| 6,544,287 B1 | 4/2003 | Johnson et al. | |
| 6,592,617 B2 * | 7/2003 | Thompson | 623/1.53 |
| 6,620,917 B1 | 9/2003 | Mello et al. | |
| 6,627,422 B1 | 9/2003 | Li et al. | |
| 6,630,414 B1 * | 10/2003 | Matsumoto | 442/1 |
| 6,638,284 B1 * | 10/2003 | Rousseau et al. | 606/151 |
| 6,645,041 B2 | 11/2003 | Sorensen | |
| 6,729,356 B1 * | 5/2004 | Baker et al. | 139/387 R |
| 6,730,016 B1 | 5/2004 | Cox et al. | |
| 6,737,371 B1 * | 5/2004 | Planck et al. | 442/304 |
| 6,773,459 B2 * | 8/2004 | Dauner et al. | 623/13.18 |
| 6,783,554 B2 * | 8/2004 | Amara et al. | 623/23.76 |
| 6,815,427 B2 | 11/2004 | Tsubouchi et al. | |
| 6,827,743 B2 * | 12/2004 | Eisermann et al. | 623/23.54 |
| 6,848,281 B2 * | 2/2005 | Ishihara et al. | 66/195 |
| 6,856,715 B1 | 2/2005 | Ebbesen et al. | |
| 6,866,681 B2 * | 3/2005 | Laboureau et al. | 623/13.2 |
| 6,875,787 B2 | 5/2005 | Donde | |
| 6,902,932 B2 * | 6/2005 | Altman et al. | 435/395 |
| 6,912,877 B2 * | 7/2005 | Yokoyama et al. | 66/195 |
| 6,946,003 B1 * | 9/2005 | Wolowacz et al. | 623/23.72 |
| 6,966,918 B1 * | 11/2005 | Schuldt-Hempe et al. | 606/151 |
| 6,971,252 B2 * | 12/2005 | Therin et al. | 66/170 |
| 7,014,807 B2 | 3/2006 | O'Brien | |
| 7,021,086 B2 * | 4/2006 | Ory et al. | 66/195 |
| 7,025,063 B2 * | 4/2006 | Snitkin et al. | 128/885 |
| 7,049,346 B1 | 5/2006 | Van Bladel et al. | |
| 7,102,577 B2 | 9/2006 | Richard et al. | |
| 7,115,388 B2 * | 10/2006 | Tsubouchi | 435/68.1 |
| 7,156,858 B2 * | 1/2007 | Schuldt-Hempe et al. | 606/151 |
| 7,166,570 B2 * | 1/2007 | Hunter et al. | 514/21.92 |
| 7,285,637 B2 * | 10/2007 | Armato et al. | 530/353 |
| 7,293,433 B1 * | 11/2007 | McMurray | 66/170 |
| 7,316,822 B2 | 1/2008 | Binette et al. | |
| 7,331,199 B2 * | 2/2008 | Ory et al. | 66/170 |
| 7,338,531 B2 * | 3/2008 | Ellis et al. | 623/23.74 |
| 7,341,601 B2 | 3/2008 | Eisermann et al. | |
| 7,404,819 B1 | 7/2008 | Darios et al. | |
| 7,418,045 B2 | 8/2008 | Willink | |
| 7,429,206 B2 | 9/2008 | Perry | |
| 7,476,249 B2 * | 1/2009 | Frank | 623/8 |
| 7,532,660 B2 | 5/2009 | Chae et al. | |

(56) References Cited

U.S. PATENT DOCUMENTS

| | | | |
|---|---|---|---|
| 7,614,258 B2* | 11/2009 | Cherok et al. | 66/192 |
| 7,635,755 B2 | 12/2009 | Kaplan et al. | |
| 7,662,409 B2 | 2/2010 | Masters | |
| 7,674,882 B2 | 3/2010 | Kaplan et al. | |
| 7,727,575 B2 | 6/2010 | Kaplan et al. | |
| 7,795,203 B2 | 9/2010 | Babizhayev | |
| 7,824,701 B2* | 11/2010 | Binette et al. | 424/423 |
| 7,828,855 B2 | 11/2010 | Ellis et al. | |
| 7,842,780 B2* | 11/2010 | Kaplan et al. | 530/324 |
| 7,875,074 B2* | 1/2011 | Chen et al. | 623/8 |
| 7,875,296 B2 | 1/2011 | Binette et al. | |
| 7,900,484 B2 | 3/2011 | Cherok et al. | |
| 8,007,531 B2* | 8/2011 | Frank | 623/8 |
| 8,157,822 B2* | 4/2012 | Browning | 606/151 |
| 8,172,901 B2 | 5/2012 | Altman et al. | |
| 8,177,834 B2* | 5/2012 | Carlson et al. | 623/1.51 |
| 8,197,542 B2* | 6/2012 | Becker | 623/8 |
| 8,202,317 B2* | 6/2012 | Becker | 623/8 |
| 8,226,715 B2* | 7/2012 | Hwang et al. | 623/13.14 |
| 8,228,347 B2 | 7/2012 | Beasley et al. | |
| 8,246,947 B2 | 8/2012 | Hedrick et al. | |
| 8,323,675 B2* | 12/2012 | Greenawalt | 424/423 |
| 8,418,508 B2* | 4/2013 | Lecuivre et al. | 66/195 |
| 8,456,711 B2 | 6/2013 | Zhang et al. | |
| 8,623,398 B2 | 1/2014 | Altman et al. | |
| 8,628,791 B2 | 1/2014 | Altman et al. | |
| 8,633,027 B2 | 1/2014 | Altman et al. | |
| 8,685,426 B2 | 4/2014 | Altman et al. | |
| 8,689,362 B2* | 4/2014 | Lavin | 2/91 |
| 8,726,700 B2* | 5/2014 | Waldman et al. | 66/171 |
| 8,746,014 B2* | 6/2014 | Mortarino | 66/170 |
| 2001/0008924 A1 | 7/2001 | Rappoport | |
| 2002/0025340 A1 | 2/2002 | Dyer | |
| 2002/0062151 A1 | 5/2002 | Altman et al. | |
| 2002/0156437 A1* | 10/2002 | McDevitt et al. | 604/290 |
| 2003/0044155 A1 | 3/2003 | Maiden | |
| 2003/0061839 A1 | 4/2003 | Kost | |
| 2003/0087433 A1* | 5/2003 | Tsubouchi et al. | 435/391 |
| 2003/0099630 A1 | 5/2003 | DiBenedetto et al. | |
| 2003/0100108 A1 | 5/2003 | Altman et al. | |
| 2003/0106346 A1* | 6/2003 | Matsumoto | 66/195 |
| 2003/0106347 A1 | 6/2003 | Kost | |
| 2003/0165548 A1* | 9/2003 | Tsubouchi et al. | 424/401 |
| 2003/0183978 A1* | 10/2003 | Asakura | 264/210.8 |
| 2003/0228815 A1 | 12/2003 | Bhatnagar et al. | |
| 2004/0005363 A1* | 1/2004 | Tsukada et al. | 424/537 |
| 2004/0029478 A1 | 2/2004 | Planck | |
| 2004/0093069 A1* | 5/2004 | Priewe et al. | 623/1.15 |
| 2004/0170827 A1* | 9/2004 | Crighton | 428/357 |
| 2004/0176658 A1* | 9/2004 | McMurray | 600/37 |
| 2004/0209538 A1 | 10/2004 | Klinge et al. | |
| 2004/0211225 A1 | 10/2004 | Dickerson | |
| 2004/0219630 A1 | 11/2004 | Tsubouchi | |
| 2004/0224406 A1 | 11/2004 | Altman et al. | |
| 2004/0235958 A1 | 11/2004 | Donde | |
| 2004/0266992 A1 | 12/2004 | Migliaresi et al. | |
| 2005/0089552 A1 | 4/2005 | Altman et al. | |
| 2005/0228408 A1* | 10/2005 | Fricke et al. | 606/151 |
| 2005/0240261 A1* | 10/2005 | Rakos et al. | 623/1.51 |
| 2005/0260706 A1* | 11/2005 | Kaplan et al. | 435/69.1 |
| 2005/0266902 A1 | 12/2005 | Khatri et al. | |
| 2005/0288797 A1* | 12/2005 | Howland | 623/23.74 |
| 2006/0009835 A1* | 1/2006 | Osborne et al. | 623/1.13 |
| 2006/0013950 A1* | 1/2006 | Porter et al. | 427/171 |
| 2006/0015184 A1 | 1/2006 | Winterbottom et al. | |
| 2006/0029578 A1 | 2/2006 | Hoemann et al. | |
| 2006/0030393 A1 | 2/2006 | Seelig et al. | |
| 2006/0030939 A1 | 2/2006 | Frank | |
| 2006/0051377 A1 | 3/2006 | First | |
| 2006/0153815 A1 | 7/2006 | Seyda et al. | |
| 2006/0205927 A1 | 9/2006 | Jin et al. | |
| 2006/0257488 A1 | 11/2006 | Hubbard | |
| 2006/0268962 A1 | 11/2006 | Cairns et al. | |
| 2006/0273279 A1 | 12/2006 | Kaplan et al. | |
| 2007/0041952 A1 | 2/2007 | Guilak et al. | |
| 2007/0071149 A1 | 3/2007 | Li et al. | |
| 2007/0088434 A1 | 4/2007 | Frank | |
| 2007/0104692 A1 | 5/2007 | Quijano et al. | |
| 2007/0104693 A1 | 5/2007 | Quijano et al. | |
| 2007/0142009 A1 | 6/2007 | Scarpa et al. | |
| 2007/0179605 A1 | 8/2007 | Myung et al. | |
| 2007/0187862 A1 | 8/2007 | Kaplan | |
| 2007/0207186 A1* | 9/2007 | Scanlon et al. | 424/424 |
| 2007/0207540 A1 | 9/2007 | Akashi | |
| 2007/0243831 A1 | 10/2007 | Seki | |
| 2008/0038236 A1* | 2/2008 | Gimble et al. | 424/93.21 |
| 2008/0075749 A1 | 3/2008 | Dyer | |
| 2008/0085272 A1 | 4/2008 | Kaplan | |
| 2008/0097601 A1 | 4/2008 | Codori-Hurff et al. | |
| 2008/0131509 A1* | 6/2008 | Hossainy et al. | 424/484 |
| 2008/0152030 A1 | 6/2008 | Abramov et al. | |
| 2008/0176960 A1 | 7/2008 | Tsukada et al. | |
| 2008/0200086 A1 | 8/2008 | Porter | |
| 2008/0206302 A1* | 8/2008 | Sittinger et al. | 424/423 |
| 2008/0228028 A1 | 9/2008 | Carlson | |
| 2008/0274161 A1 | 11/2008 | Muratoglu et al. | |
| 2008/0293919 A1 | 11/2008 | Kaplan et al. | |
| 2008/0300681 A1 | 12/2008 | Rigotti et al. | |
| 2008/0300683 A1* | 12/2008 | Altman et al. | 623/13.11 |
| 2008/0306681 A1 | 12/2008 | Piwowarski et al. | |
| 2009/0004737 A1 | 1/2009 | Borenstein et al. | |
| 2009/0024162 A1* | 1/2009 | Shalaby et al. | 606/230 |
| 2009/0030454 A1* | 1/2009 | Knight et al. | 606/230 |
| 2009/0171467 A1 | 7/2009 | Mann et al. | |
| 2009/0181104 A1 | 7/2009 | Rigotti | |
| 2009/0202614 A1 | 8/2009 | Kaplan et al. | |
| 2009/0214649 A1* | 8/2009 | Gazit et al. | 424/484 |
| 2009/0232963 A1 | 9/2009 | Kaplan et al. | |
| 2009/0245408 A1 | 10/2009 | Mujtaba et al. | |
| 2009/0317376 A1 | 12/2009 | Zukowska et al. | |
| 2010/0023029 A1* | 1/2010 | Young | 606/151 |
| 2010/0028451 A1 | 2/2010 | Kaplan et al. | |
| 2010/0046902 A1 | 2/2010 | Kaplan et al. | |
| 2010/0055438 A1 | 3/2010 | Kaplan et al. | |
| 2010/0063404 A1 | 3/2010 | Kaplan et al. | |
| 2010/0065784 A1 | 3/2010 | Kaplan et al. | |
| 2010/0069017 A1 | 3/2010 | Yamamoto et al. | |
| 2010/0070068 A1 | 3/2010 | Kaplan et al. | |
| 2010/0096763 A1 | 4/2010 | Kaplan et al. | |
| 2010/0120116 A1 | 5/2010 | Kaplan et al. | |
| 2010/0143487 A1 | 6/2010 | Masters | |
| 2010/0145367 A1* | 6/2010 | Ratcliffe | 606/151 |
| 2010/0160948 A1 | 6/2010 | Rigotti et al. | |
| 2010/0161052 A1 | 6/2010 | Rigotti et al. | |
| 2010/0168780 A1 | 7/2010 | Rigotti et al. | |
| 2010/0191328 A1 | 7/2010 | Kaplan et al. | |
| 2010/0196447 A1 | 8/2010 | Kaplan et al. | |
| 2010/0196478 A1 | 8/2010 | Masters | |
| 2010/0203226 A1 | 8/2010 | Kaplan et al. | |
| 2010/0209405 A1 | 8/2010 | Altman et al. | |
| 2010/0233267 A1 | 9/2010 | Chen et al. | |
| 2010/0249024 A1* | 9/2010 | Powell et al. | 623/8 |
| 2010/0256756 A1 | 10/2010 | Altman et al. | |
| 2010/0278405 A1 | 11/2010 | Kakadiaris et al. | |
| 2011/0008406 A1 | 1/2011 | Altman et al. | |
| 2011/0008436 A1 | 1/2011 | Altman et al. | |
| 2011/0008437 A1 | 1/2011 | Altman et al. | |
| 2011/0009960 A1* | 1/2011 | Altman et al. | 623/8 |
| 2011/0014263 A1 | 1/2011 | Altman et al. | |
| 2011/0014287 A1 | 1/2011 | Altman et al. | |
| 2011/0020409 A1 | 1/2011 | Altman et al. | |
| 2011/0022171 A1* | 1/2011 | Richter et al. | 623/8 |
| 2011/0052695 A1 | 3/2011 | Jiang et al. | |
| 2011/0054604 A1 | 3/2011 | Becker | |
| 2011/0054605 A1 | 3/2011 | Becker | |
| 2011/0070281 A1 | 3/2011 | Altman et al. | |
| 2011/0097381 A1 | 4/2011 | Binette | |
| 2011/0106249 A1* | 5/2011 | Becker | 623/8 |
| 2011/0111031 A1 | 5/2011 | Jiang et al. | |
| 2011/0129531 A1 | 6/2011 | Collette et al. | |
| 2011/0143673 A1 | 6/2011 | Landesman et al. | |
| 2011/0150846 A1 | 6/2011 | Van Epps et al. | |
| 2011/0167602 A1 | 7/2011 | Altman et al. | |
| 2011/0171239 A1 | 7/2011 | Kaplan et al. | |

(56) References Cited

U.S. PATENT DOCUMENTS

| | | | |
|---|---|---|---|
| 2011/0171453 A1 | 7/2011 | Altman et al. | |
| 2011/0183001 A1 | 7/2011 | Rosson et al. | |
| 2011/0184227 A1* | 7/2011 | Altman et al. | 600/37 |
| 2011/0189292 A1 | 8/2011 | Lebreton et al. | |
| 2011/0189773 A1 | 8/2011 | Altman et al. | |
| 2011/0190795 A1* | 8/2011 | Hotter et al. | 606/151 |
| 2011/0224703 A1* | 9/2011 | Mortarino | 606/151 |
| 2011/0257665 A1* | 10/2011 | Mortarino | 606/151 |
| 2011/0257761 A1* | 10/2011 | Mortarino | 623/23.72 |
| 2011/0282365 A1* | 11/2011 | Hadba et al. | 606/151 |
| 2011/0301717 A1 | 12/2011 | Becker | |
| 2012/0045420 A1 | 2/2012 | Van Epps et al. | |
| 2012/0053690 A1 | 3/2012 | Frank | |
| 2012/0164116 A1 | 6/2012 | Van Epps et al. | |
| 2012/0165935 A1 | 6/2012 | Van Epps | |
| 2012/0165957 A1* | 6/2012 | Everland et al. | 623/23.72 |
| 2012/0171265 A1 | 7/2012 | Altman et al. | |
| 2012/0172317 A1 | 7/2012 | Altman et al. | |
| 2012/0172985 A1 | 7/2012 | Altman et al. | |
| 2012/0184974 A1* | 7/2012 | Becker | 606/151 |
| 2012/0207837 A1 | 8/2012 | Powell et al. | |
| 2012/0209381 A1 | 8/2012 | Powell et al. | |
| 2012/0213852 A1 | 8/2012 | Van Epps et al. | |
| 2012/0213853 A1 | 8/2012 | Van Epps et al. | |
| 2012/0219627 A1 | 8/2012 | Van Epps et al. | |
| 2012/0226352 A1* | 9/2012 | Becker | 623/8 |
| 2012/0244143 A1* | 9/2012 | Lo et al. | 424/130.1 |
| 2012/0263686 A1 | 10/2012 | Van Epps et al. | |
| 2012/0265297 A1 | 10/2012 | Altman et al. | |
| 2012/0269777 A1 | 10/2012 | Van Epps et al. | |
| 2015/0148823 A1* | 5/2015 | Mortarino et al. | 606/151 |

FOREIGN PATENT DOCUMENTS

| | | |
|---|---|---|
| DE | 19928635 | 10/2000 |
| EP | 0677297 A1 | 10/1995 |
| EP | 1241178 A1 | 9/2002 |
| EP | 0889156 B1 | 8/2003 |
| EP | 1493404 A1 | 1/2005 |
| EP | 2016956 A2 | 1/2009 |
| EP | 2210971 A1 | 7/2010 |
| EP | 2068766 B1 | 10/2011 |
| JP | 06-245989 | 9/1994 |
| JP | 08295697 A | 11/1996 |
| WO | 9525550 A1 | 9/1995 |
| WO | 9708315 A1 | 3/1997 |
| WO | 9825653 A2 | 6/1998 |
| WO | 016811 A1 | 3/2000 |
| WO | 0057812 A1 | 10/2000 |
| WO | 0072782 A1 | 12/2000 |
| WO | 0187267 A1 | 11/2001 |
| WO | 0229141 A1 | 4/2002 |
| WO | 03022909 A1 | 3/2003 |
| WO | 2004062697 A2 | 7/2004 |
| WO | 2004080346 A2 | 9/2004 |
| WO | 2005123114 A2 | 12/2005 |
| WO | 2006017834 A2 | 2/2006 |
| WO | 2006102477 A2 | 9/2006 |
| WO | 2008016919 A2 | 2/2008 |
| WO | 2008042992 A2 | 4/2008 |
| WO | 2008106485 A2 | 9/2008 |
| WO | 2008116127 A2 | 9/2008 |
| WO | 2008148071 A2 | 12/2008 |
| WO | 2009003135 A1 | 12/2008 |
| WO | 2009023615 A1 | 2/2009 |
| WO | 2010074827 A2 | 7/2010 |
| WO | 2010141133 A2 | 12/2010 |
| WO | 2011031854 A1 | 3/2011 |
| WO | 2014138226 A1 | 9/2014 |

OTHER PUBLICATIONS

Altman, et al., Silk Fibers and Materials—Properties and Processing, Nov. 26, 2001, Tufts University.
Altman, Gregory et al., Silk-Based Biomaterials, Biomaterials, 2003, 401-416, 24.
Altman, Gregory H., Silk Matrix for Tissue Engineered Anterior Cruciate Ligaments, Biomaterials, Apr. 26, 2002, 4131-4141, 23, Elsevier, US.
Azimzadeh, A. et al., Xenograft rejection: modular mechanisms and therapeutic prospects, Hematology and Cell Therapy, 1997, 331-343, 38(4).
Belousova, Natalya et al., Modulation of Adenovirus Vector Tropism Via Incorporation of Polypeptide Ligands Into the Fiber Protein, Journal of Virology, Sep. 2002, 8621-8631, 76 (17), US.
Cao, Yang et al., Biodegradation of Silk Biomaterials, Int. J. Mol. Sci., 2009, 1514-1524, 10.
Caplan, et al., Mesenchymal Stem Cells and Tissue Repair, The Anterior Cruciate Ligament: Current and Future Concepts, 1993, 405-417, Chapter 36, Raven Press, Ltd., New York.
Chen et al., Materials design analysis of the prosthetic anterior cruciate ligament, Journal of Biomedical Materials Research, 1980, 567-586, vol. 14.
Dunn, et al., Anterior cruciate ligament reconstruction using a composite collagenous prosthesis, The American Journal of Sports Medicine, 1992, 507-515, vol. 20, No. 5.
Dunn, Michael G., Tissue-Engineering Strategies for Ligament Reconstruction, MRS Bulletin, Nov. 1996, 43-46.
Erli, Hans J. et al., Surface Pretreatments for Medical Application of Adhesion, Biomedical Engineering Online, 2003, 15, 2, US.
Gamboa-Bobadilla, Mabel et al., Implant Breast Reconstruction Using Acellular Dermal Matrix, Ann Plast Surg, 2006, 22-25, 56.
Gil, Eun S. et al., Effect of Beta-Sheet Crystals on the Thermal and Rheological Behavior of Protein-Based Hydrogels Derived From Gelatin and Silk Fibroin, Macromolecular Bioscience, 2005, 702-709, 5 (8), US.
Goes, et al., Immediate Reconstruction After Skin-sparing Mastectomy Using the Omental Flap and Synthetic Mesh, The Surgery of the Breast, Principles and Art, 2006, 786-793, 2nd Edition, Chapter 52, Lippincott Williams & Wilkins.
Gosline et al., the Mechanical Design of Spider Silks: from Fibroin Sequence to Mechanical Function, The Journal of Experimental Biology, 1999, 3295-3303, 202, The Company of Biologists Limited, GB.
Gould, Dina et al., Direct and indirect recognition: the role of MHC antigens in graft rejection, Immunology Today, 1999, 77-82, 20(2).
Goulet et al., The Need for Bioengineered Tendons and Ligaments, Principles of Tissue Engineering, 1997, 633-644, Chapter 39, R.G. Landes Company.
Gulsen et al., Ophthalmic Drug Delivery Through Contact Lenses, Investigative Opthamology & Visual Science, 2004, 2342-2347, 45(7), Association for Research in Vision and Opthamology.
Hersel, Ulrich et al., RGD Modified Polymers: Biomaterials for Stimulated Cell Adhesion and Beyond, Biomaterials, 2003, 4385-4415, 24, Elsevier, US.
Hinman et al., Synthetic spider silk: a modular fiber, Tibtech, Sep. 2000, 374-379, 18, Elsevier Science Ltd.
Hoechst Celanese, Dictionary of Fiber & Textile Technology, 1990, 140-141.
Holmes, F.H., Sedimentation and Diffusion of Soluble Fibroin, Nature, Feb. 2, 1952, 193, 4292.
Horan, R.L. et al., Biological and Biomechanical Assessment of a Long-Tem, Bioresorbable Silk-Derived Surgical Mesh in an Abdominal Body Wall Defect Model, Hernia, 2009, 189-199, 13.
Horan, Rebecca et al, in Vitro Degradation of Silk Fibroin, Biomaterials, 2005, 3385-3393, 26.
Kardestuncer, T. et al., RGD-Tethered Silk Substrate Stimulates the Differentiation of Human Tendon Cells, Clinical Orthopaedics and Related Research, 2006, 234-239, 448.
Kurosaki, Sadayuki et al., Fibroin Allergy IgE Mediated Hypersensitivity to Silk Suture Materials, Journal of Nippon Medical School, 1999, 41-44, 66 (1), JP.
Langer et al., Tissue Engineering, Science, May 14, 1993, 920-926, 260.
Loebsack, Anna, in Vivo Characterization of a Porous Hydrogel Material for Use as a Tissue Bulking Agent, J Biomed Mater Res, 2001, 575-581, 57.

(56) References Cited

OTHER PUBLICATIONS

Markolf et al., Instrumented Measurements of Laxity in Patients Who Have a Gore-Tex Anterior Cruciate-Ligament Substitute, The Journal of Bone and Joint Surgery, Jul. 1989, 887-893, vol. 71A, No. 6.

Millipore, https://www.millipore.com/userguides/tech1/www-uf; 2005.

Numata, Keiji et al., Bioengineered Silk Protein-Based Gene Delivery Systems, Biomaterials, 2009, 5775-5784, 30.

Panilaitis, Bruce et al., Macrophage Responses to Silk, Biomaterials, 2003, 3079-3085, 24.

Patel, Parul Natvar, Materials Employed for Breast Augmentation and Reconstruction, Scaffolding in Tissue Engineering, 2006, 425-436, Chapter 28.

Perez-Rigueiro et al., Silkworm Silk as an Engineering Material, Journal of Applied Polymer Science, 1998, 2439-2447, vol. 70.

Phillips, David et al., Dissolution and Regeneration of Bombyx Mod Silk Fibroin Using Ionic Liquids, Journal of the American Chemical Society, 2004, 14350-14351, 126.

Santin et al., in vitro evaluation of the inflammatory potential of the silk fibroin, Feb. 4, 1999, 382-389, John Wiley & Sons, Inc.

Servoli Eva et al., Surface Properties of Silk Fibroin Films and Their Interaction with Fibroblasts, Macromolecular Bioscience, 2005, 1175-1183, 5.

Shoemaker et al., The Limits of Knee Motion, in Vitro Studies, Knee Ligaments: Structure, Function, Injury, and Repair, 1990, 153-161, Chapter 9, Raven Press, Ltd.

Sigma-Aldrich, Surfactants Classified by HLB Numbers, 2011, Retrieve: Nov. 19, 2011, 5 pages. http://www.sigmaaldrich.com/materials-science/material-science-products.printerview.html.

Sofia, Susan, Functionalized silk-based biomaterials for bone formation, Journal of Biomedical Materials Research, 2000, 139-148, 54.

Sohn, Sungkyun et al., Phase Behavior and Hydration of Silk Fibroin, Biomacromolecules, 2004, 751-757, 5.

Sussman, Mark, Hearts and Bones, Nature, Apr. 5, 2001, 640-641, 410, Macmillan Magazines Ltd.

Tamada, Yasushi, Cell Adhesion and Growth on Various Kinds of Silk Fabrics, Sen'i Gakkai Symposia Preprints, 1998, 2 Pages, JP.

Tsukada, Masuhiro et al., Preparation and Application of Porous Silk Fibroin Materials, Journal of Applied Polymer Science, 1994, 507-514, 54.

Vepari, Charu et al., Silk as a Biomaterial, Prog. Polym. Sci., 2007, 991-1007, 32.

Wang et al., Cartilage tissue engineering with silk scaffolds and human articular chondrocytes, Biomaterials, 2006, 4434-4442, 27, Elsevier.

Wang, Yongzhong et al., Stem Cell-Based Tissue Engineering with Silk Biomaterials, Biomaterials, 2006, 6064-6082, 27.

Woo et al., The Tensile Properties of Human Anterior Cruciate Ligament (ACL) and ACL Graft Tissues, Knee Ligaments: Structure, Function, Injury, and Repair, 1990, 279-289, Chapter 13, Raven Press, Ltd.

Woods et al., The Gore-Tex anterior cruciate ligament prosthesis, The American Journal of Sports Medicine, 1991, 48-55, vol. 19, No. 1.

Xu et al., Structure of a protein superfiber: Spider dragline silk, Proc. Nat. Acad. Sci., Sep. 1990, 7120-7124, 87.

Yoo, Hyuk Sang et al., Hyaluronic Acid Modified Biodegradable Scaffolds for Cartilage Tissue Engineering, Biomatenals, 2005, 1925-1933, 26.

Young et al., Use of Mesenchymal Stem Cells in a Collagen Matrix for Achilles Tendon Repair, Journal of Orthopaedic Research, 1998, 406-413, 16.

Zhao et al., Structural Characterization and Artificial Fiber Formation of Bombyx mori Silk Fibroin in Hexafluoro-lso-Propanol Solvent System, Biopolymers, 2003, 253-259, 69, Wiley Periodicals, Inc.

Zhu, Zhenghua et al., Preparation and Characterization of Regenerated Bombyx Mod Silk Fibroin Fiber Containing Recombinant Cell-Adhesive Proteins; Nonwoven Fiber and Monofilament, J. Appl. Polym. Sci., 2008, 2956-2963, 109.

Zocchi, M.L. et al., Bicompartmental Breast Lipostructuring, Aesth Plast Surg, 2008, 313-328, 32.

* cited by examiner

Fig 1K

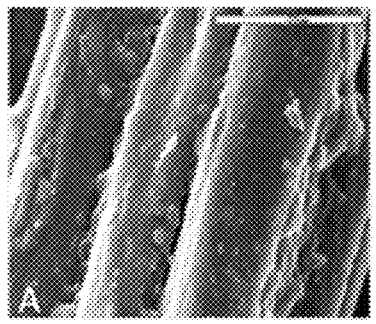 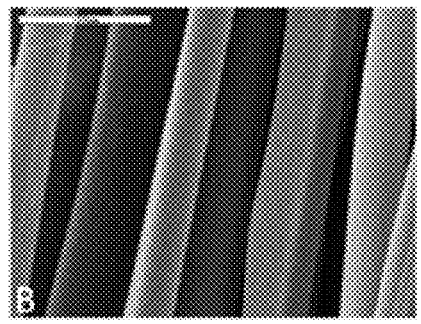
FIGURE 3A  FIGURE 3B
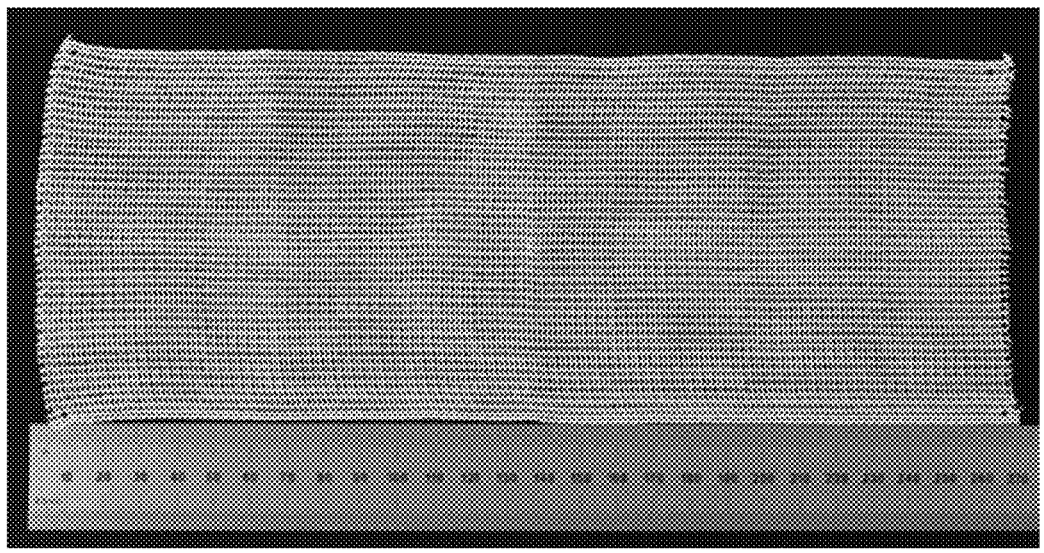
Figure 4

PLIABLE SILK MEDICAL DEVICE

CROSS REFERENCE

This patent application is a continuation in part of U.S. patent application Ser. No. 13/715,872, filed Dec. 14, 2012, which is a continuation in part of U.S. patent application Ser. No. 13/306,325, filed Nov. 29, 2011, which is a continuation in part of U.S. patent application Ser. No. 13/186,151, filed Jul. 19, 2011, which is a continuation in part of U.S. patent application Ser. No. 13/156,283, filed Jun. 8, 2011, which is a continuation in part of U.S. patent application Ser. No. 12/680,404, filed Sep. 19, 2011, which is a national stage entry of PCT patent application number PCT/US09/63717, filed Nov. 9, 2009, which claims priority to and the benefit of United States provisional patent application No. 61/122,520, filed Dec. 15, 2008, all of which applications are expressly incorporated by reference herein in their entireties.

BACKGROUND

The present invention is a biodegradable (synonymously bioresorbable), biocompatible, pliable, knitted silk matrix, mesh or scaffold (the "device") and methods for making and using the device in surgical and cosmetic procedures where soft tissue (i.e. a gland, organ, muscle, skin, ligament, tendon, cartilage, blood vessel or mesentery) support (through the load bearing function of the device) is desired, such as for example in breast reconstruction, breast augmentation, abdominal surgery, gastro-intestinal surgery, hernia repair and facial surgery. The soft tissue support can be provided by the device itself (for example in conjunction with a hernia repair) or by the device being used in conjunction with another implant, for example use of the device on or around a tissue expander or a breast implant used in a breast reconstruction or a breast augmentation surgical procedure.

Soft tissue support surgical meshes and scaffolds are known and are usually made of a synthetic polymer such as Teflon®, polypropylene, polyglycolic acid, polyester, or polyglactin 910. Biomaterials such a tissue based or tissue derived material, for example an acellular dermal matrix ("ADM") obtained from human and animal derived dermis have also been used but do not have the mechanical integrity of high load demand applications (e.g. ligaments, tendons, muscle) or the appropriate biological functionality because most biomaterials either degrade too rapidly (e.g., collagen, PLA, PGA, or related copolymers) or are non-degradable (e.g., polyesters, metal), and in either case functional autologous tissue ingrowth (important to assist transfer of a load bearing function from an implanted biomaterial as the biomaterial is bioresorbed by the body) occurs very little or fails to occur. In certain instances a biomaterial may misdirect tissue differentiation and development (e.g. spontaneous bone formation, tumors) because it lacks biocompatibility with surrounding cells and tissue. As well, a biomaterial that fails to degrade typically is associated with chronic inflammation and such a response is detrimental to (i.e. weakens) surrounding and adjacent tissue.

Silk is a natural (non-synthetic) protein made of high strength fibroin fibers with mechanical properties similar to or better than many of synthetic high performance fibers. Silk is also stable at physiological temperatures in a wide range of pH, and is insoluble in most aqueous and organic solvents. As a protein, unlike the case with most if not all synthetic polymers, the degradation products (e.g. peptides, amino acids) of silk are biocompatible. Silk is non-mammalian derived and carries far less bioburden than other comparable natural biomaterials (e.g. bovine or porcine derived collagen). Silk, as the term is generally known in the art, means a filamentous fiber product secreted by an organism such as a silkworm or spider. Silks can be made by certain insects such as for example *Bombyx mori* silkworms, and *Nephilia clavipes* spiders. There are many variants of natural silk. Fibroin is produced and secreted by a silkworm's two silk glands. As fibroin leaves the glands it is coated with sericin a glue-like substance. Spider silk s produced as a single filament lacking the immunogenic protein sericin. Use of both silkworm silk and spider silk (from a natural source or made recombinantly) is within the scope of the present invention.

Silkworm silk has been used in biomedical applications. The *Bombyx mori* species of silkworm produces a silk fiber (a "bave") and uses the fiber to build its cocoon. The bave as produced include two fibroin filaments or broins which are surrounded with a coating of the gummy, antigenic protein sericin. Silk fibers harvested for making textiles, sutures and clothing are not sericin extracted or are sericin depleted or only to a minor extent and typically the silk remains at least 10% to 26% by weight sericin. Retaining the sericin coating protects the frail fibroin filaments from fraying during textile manufacture. Hence textile grade silk is generally made of sericin coated silk fibroin fibers. Medical grade silkworm silk is used as either as virgin silk suture, where the sericin has not been removed, or as a silk suture from which the sericin has been removed and replaced with a wax or silicone coating to provide a barrier between the silk fibroin and the body tissue and cells. Physicians prefer and require an implantable, knitted silk medical device with the flexibility to be stretched, expanded, pulled into shape, elongated and/or draped into place over, around or under soft tissue or an implant at the time of a soft tissue surgical or medical procedure, without the silk medical device upon its elongation breaking, splitting or unraveling. Thus there is a need for such a pliable, sericin extracted implantable, bioresorbable silk medical device.

SUMMARY

A device according to the present invention fulfills this need. The device in one embodiment is a pliable. knitted mesh having at least two yarns laid in a knit direction and engaging each other to define a plurality of nodes, the at least two yarns including a first yarn and a second yarn extending between and forming loops about two nodes, the second yarn having a higher tension at the two nodes than the first yarn, the second yarn substantially preventing the first yarn from moving at the two nodes and substantially preventing the knitted mesh from unraveling at the nodes. The device is a surgical mesh made of silk that is knitted, multi-filament, and bioengineered. It is mechanically strong, biocompatible, and long-term bioresorbable. The sericin-extracted silkworm fibroin fibers of the device retain their native protein structure and have not been dissolved and/or reconstituted.

"Bioresorbed" means that none or fewer than 10% of the silk fibroin fibers of the device can be seen to the naked (no magnification aid) eye upon visual inspection of the site of implantation of the device or of a biopsy specimen therefrom, and/or that the device is not palpable (i.e. cannot be felt by a surgeon at a time after the surgery during which the device was implanted) upon tactile manipulation of the dermal location of the patient at which the device was implanted. Typically either or both of these bioresorbed determinants occur about 1 to about 5 years are in vivo implantation of the device.

"About" means plus or minus ten percent of the quantify, number, range or parameter so qualified.

The device of the present invention is a pliable, sterile surgical mesh or scaffold available in a variety of shapes and sizes ready for use in open surgical or in laparoscopic procedures. The device is flexible and well-suited for delivery through a laparoscopic trocar due to its strength, tear resistance, suture retention, and ability to be cut in any direction. The device can provide immediate physical and mechanical stabilization of a tissue defect through the strength and porous (scaffold-like) construction of the device. The device can be used as a transitory scaffold for soft tissue support and repair to reinforce deficiencies where weakness or voids exist that require the addition of material to obtain the desired surgical outcome.

The device can comprise filament twisted silk yarns. The silk is made of silk fibroin fibers. The silk fibroin fibers are preferably sericin depleted or sericin extracted silk fibroin fibers. The device has an open pore knit structure. Significantly, after implantation the device and ingrown native tissue can maintain at least about 90% of the time zero device strength of the device at one month or at three months or at six months in vivo after the implantation. The device can be implanted without regard to side orientation of the device and the combined thickness of the device and ingrowth of native tissue scaffold increases with time in vivo in the patient.

As used herein, "fibroin" includes silkworm fibroin (i.e. from *Bombyx mori*) and fibroin-like fibers obtained from spiders (i.e. from *Nephila clavipes*). Alternatively, silk protein suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012.

The device is a pliable, knitted silk fabric intended for implantation in a human body. The word "knit" is synonymous with the word "knitted", so that a knit silk fabric is the same as a knitted silk fabric. The device can be a warp knit or can be weft knit silk fabric. Preferably, the device according of the present invention is a pliable, biocompatible, warp knit, multi-filament silk fabric. A woven material or fabric is made by weaving, which is a process that does not use needles, and results in a fabric with different characteristics. In particular, a woven fabric is made by a non-needle process using multiple yarns that interlace each other at right angles to form a structure wherein one set of yarn is parallel to the direction of fabric formation. Woven fabrics are classified as to weave or structure according to the manner in which warp and weft cross each other. The three main types of weaves (woven fabrics) are plain, twill, and satin. Woven (weaved) silk fabric, woven textiles and woven fabrics are not within the scope of the present invention. Non-woven fabrics are also not within the scope of the present invention. Non-woven (also refer to as bonded) fabrics are formed by having multiple fibers cohered together chemically or physically, without use of needles.

Unlike the excluded woven and non-woven materials, a knitted fabric is generally softer and more supple because its thread is treated differently. Thus a knitted fabric is made by using needles (such as for example the needles of a single or double bed knit machine) to pull threads up through the preceding thread formed into a loop by the needle. Because a knitted fabric is made using needles the knitted fabric can have one or multiple yarn intermeshing (also referred as interloping). Preferably, the device is made of biodegradable silk and is a biocompatible, non-woven, knit, multi-filament silk fabric or mesh.

Embodiments according to aspects of the present invention provide a biocompatible surgical silk mesh device for use in soft or hard tissue repair. Examples of soft tissue repair include hernia repair, rotator cuff repair, cosmetic surgery, implementation of a bladder sling, or the like. Examples of hard tissue repair, such as bone repair, involve reconstructive plastic surgery, ortho trauma, or the like.

Advantageously, the open structure of the device allows tissue ingrowth as the silk forming the device is bioresorbed, at a rate permitting smooth transfer of mechanical properties to the new tissue from the device. Furthermore, the device has a knit pattern that substantially or entirely prevents unraveling, especially when the device is cut. The device have a stable knit pattern made by knitting silk yarn with variations of tension between at least two yarns laid in a knit direction. For example, a first yarn and a second yarn may be laid in a knit direction to form "nodes" for a mesh device. The knit direction for the at least two yarns, for example, may be vertical during warp knitting or horizontal during weft knitting. The nodes of a mesh device, also known as intermesh loops, refer to intersections in the mesh device where the two yarns form a loop around a knitting needle. In some embodiments, the first yarn is applied to include greater slack than the second yarn, so that, when a load is applied to the mesh device, the first yarn is under a lower tension than the second device. A load that places the at least two yarns under tension may result, for example, when the mesh device is sutured or if there is pulling on the mesh device. The slack in the first yarn causes the first yarn to be effectively larger in diameter than the second yarn, so that the first yarn experiences greater frictional contact with the second yarn at a node and cannot move, or is "locked," relative to the second yarn. Accordingly, this particular knit design may be referred to as a "node-lock" design.

The device bioresorbs at a rate sufficient that allows tissue in-growth while transferring the load-bearing responsibility to the native tissue. An embodiment of the device can be made from *Bombyx mori* silkworm silk fibroin or from spider silk. The raw silk fibers have a natural globular protein coating known as sericin, which may have antigenic properties and must be depleted before implantation. Accordingly, the yarn is taken through a depletion process as described, for example, by Gregory H. Altman et al., "Silk matrix for tissue engineered anterior cruciate ligaments," Biomaterials 23 (2002), pp. 4131-4141, the contents of which are incorporated herein by reference. As a result, the silk material used in the device embodiments contains substantially no (less than 5%) sericin.

A process for making the pliable, knitted silk mesh (and for obtaining the mesh) can have the steps of: knitting a first silk yarn in a first wale direction using the knit pattern 3/1-1/1-1/3-3/3; knitting a second silk yarn in a second wale direction using the knit pattern 1/1-1/3-3/3-3/1; knitting a third silk yarn in a first course direction using the knit pattern 3/3-3/3-5/5-5/5-3/3-3/3-5/5-5/5-1/1-1/1-5/5-5/5-3/3-3/3-5/5-5/5-3/3-3/3-7/7-7/7, and; knitting a fourth silk yarn in a second course direction using the knit pattern 1/1-5/5-5/5-3/3-3/3-5/5-5/5-3/3-3/3-7/7-7/7-3/3-3/3-5/5-5/5-3/3-3/3-5/5-5/5-1/1, thereby obtaining the pliable knitted silk mesh. In this process the two movements in the wale direction occur on separate needle beds, with alternate yarns, and with loops formed on the course movements staggered within the repeat knit pattern. In this process of claim 1 the silk yarns can be made of a nine filament, twisted, and sericin depleted silk fibers, and the yarns can be made with three ends of Td 20/22 raw silk twisted together in the S direction to form a ply with 20 tpi and further combining 3 of the resulting ply with 10 tpi in the Z direction. Additionally, the e stitch density or pick count for silk mesh design can be about 40 picks per centimeter including the total picks count for the technical front face and the technical back face of the mesh, or equivalently about 20 picks per cm considering only one face of the mesh.

A detailed process for making the pliable knitted silk mesh, the process can have the steps of: knitting a first silk yarn in a first wale direction using the pattern 3/1-1/1-1/3-3/3; knitting a second silk yarn in a second wale direction using the pattern 1/1-1/3-3/3-3/3-3/1; knitting a third silk yarn in a first course direction using the pattern 3/3-3/3-5/5-5/5-3/3-3/3-5/5-5/5-1/1-1/1-5/5-5/5-3/3-3/3-5/5-5/5-3/3-3/3-7/7-7/7, and; knitting a fourth silk yarn in a second course direction using the pattern 1/1-5/5-5/5-3/3-3/3-5/5-5/5-3/3-3/3-7/7-7/7-3/3-3/3-5/5-5/5-3/3-3/3-5/5-5/5-1/1, wherein: the two movements in the wale direction occur on separate needle beds with alternate yarns and loops that occur on every course are staggered within repeat; the silk yarns are made of a nine filament, twisted, and sericin depleted silk fibers; the yarns are made with 3 ends of Td 20/22 ra(g) w silk twisted together in the S direction to form a ply with 20 tpi and further combining 3 of the resulting ply with 10 tpi in the Z direction, and; the stitch density or pick count for silk mesh design is 40 picks per centimeter including the total picks count for the technical front face and the technical back face of the mesh, or equivalently 20 picks per cm considering only one face of the mesh, thereby obtaining the pliable knitted silk mesh.

The pliable, knitted silk mesh can have percent elongation at break of between about 4% or 32% to about 109% or 110%, a burst strength of about 0.45 MPa, and a stiffness of about 25 N/mm.

A process for making a pliable, knitted silk mesh, the process comprising the steps of: knitting a first silk yarn in a first wale direction using the knit pattern 3/1-1/1-1/3-3/3; knitting a second silk yarn in a second wale direction using the knit pattern 1/1-1/3-3/3-3/1, knitting a third silk yarn in a first course direction using the knit pattern 3/3-3/3-5/5-5/5-3/3-3/3-5/5-5/5-1/1-1/1-5/5-5/5-3/3-3/3-5/5-5/5-3/3-3/3-7/7-7/7, and; knitting a fourth silk yarn in a second course direction using the knit pattern 1/1-5/5-5/5-3/3-3/3-5/5-5/5-3/3-3/3-7/7-7/7-3/3-3/3-5/5-5/5-3/3-3/3-5/5-5/5-1/1, thereby obtaining the pliable knitted silk mesh. Additionally, in this just set forth process in this paragraph: (a) the two movements in the wale direction occur on separate needle beds (a knitting machine having two needle beds); and (b) with alternate yarns such as they knit with the opposing needle bed to their location (the front set of yarn knit with the back needle bed and the back set of yarn knit with the front needle bed). Furthermore, in this just set forth in this paragraph process the silk yarns are made of a nine filaments ("filaments" can be defined as raw silk yarn having a finesse of about Td 20/22) of twisted, and sericin depleted silk fibers. Finally, in this just set forth in this paragraph process the yarns are made with three ends of raw silk yarn twisted together having a finesse of Td 20/22 twisted together in the S direction (clockwise direction of twist) to form a ply with 20 tpi (twist per inch is the number of twist measured in an inch of yarn) and further combining 3 of the resulting ply with 10 tpi in the Z direction(counter clockwise direction of twist), and the stitch density or pick count for silk mesh design is about 40 picks per centimeter including the total picks count for the technical front face and the technical back face of the mesh, or equivalently about 20 picks per cm considering only one face of the mesh.

[21] Our invention also includes a process for making a pliable knitted silk mesh, the process comprising the steps of: knitting a first silk yarn in a first wale direction using the pattern 3/1-1/1-1/3-3/3; knitting a second silk yarn in a second wale direction using the pattern 1/1-1/3-3/3-3/1, knitting a third silk yarn in a first course direction using the pattern 3/3-3/3-5/5-5/5-3/3-3/3-5/5-5/5-1/1 -1/1 -5/5-5/5-3/3-3/3-5/5-5/5-3/3-3/3-7/7-7/7, and; knitting a fourth silk yarn in a second course direction using the pattern 1/1 -5/5-5/5-3/3-3/3-5/5-5/5-3/3-3/3-7/7-7/7-3/3-3/3-5/5-5/5-3/3-3/3-5/5-5/5-1/1, wherein: (e) the two movements in the wale direction occur on separate needle beds with alternate yarns and loops that occur on every course are staggered within repeat; (f) the silk yarns are made of a nine filament, twisted, and sericin depleted silk fibers; (g) the yarns are made with 3 ends of Td 20/22 raw silk twisted together in the S direction to form a ply with 20 tpi and further combining 3 of the resulting ply with 10 tpi in the Z direction, and (h) the stitch density or pick count for silk mesh design is 40 picks per centimeter including the total picks count for the technical front face and the technical back face of the mesh, or equivalently 20 picks per cm considering only one face of the mesh, thereby obtaining the pliable knitted silk mesh.

Our invention also includes a pliable knitted silk mesh made by: knitting a first silk yarn in a first wale direction using the pattern 3/1-1/1-1/3-3/3; knitting a second silk yarn in a second wale direction using the pattern 1/1-1/3-3/3-3/1, knitting a third silk yarn in a first course direction using the pattern 3/3-3/3-5/5-5/5-3/3-3/3-5/5-5/5-1/1 -1/1 -5/5-5/5-3/3-3/3-5/5-5/5-3/3-3/3-7/7-7/7, and; knitting a fourth silk yarn in a second course direction using the pattern 1/1-5/5-5/5-3/3-3/3-5/5-5/5-3/3-3/3-7/7-7/7-3/3-3/3-5/5-5/5-3/3-3/3-5/5-5/5-1/1. With this pliable knitted silk mesh of the two movements in the wale direction occur on separate needle beds with alternate yarns and loops that occur on every course are staggered within repeat, and; the silk yarns are made of a nine filament, twisted, and sericin depleted silk fibers, and; the yarns are made with 3 ends of Td 20/22 raw silk twisted together in the S direction to form a ply with 20 tpi and further combining 3 of the resulting ply with 10 tpi in the Z direction, and; the stitch density or pick count for silk mesh design is 40 picks per centimeter including the total picks count for the technical front face and the technical back face of the mesh, or equivalently 20 picks per cm considering only one face of the mesh.

Our invention also includes a pliable knitted silk mesh made by: knitting a first silk yarn in a first wale direction using the pattern 3/1-1/1-1/3-3/3; knitting a second silk yarn in a second wale direction using the pattern 1/1-1/3-3/3-3/1, knitting a third silk yarn in a first course direction using the pattern 3/3-3/3-5/5-5/5-3/3-3/3-5/5-5/5-1/1-1/1-5/5-5/5-3/3-3/3-5/5-5/5-3/3-3/3-7/7-7/7, and; knitting a fourth silk yarn in a second course direction using the pattern 1/1-5/5-5/5-3/3-3/3-5/5-5/5-3/3-3/3-7/7-7/7-3/3-3/3-5/5-5/5-3/3-3/3-5/5-5/5-1/1, wherein: (e) the two movements in the wale direction occur on separate needle beds with alternate yarns and loops that occur on every course are staggered within repeat; (f) the silk yarns are made of a nine filament, twisted, and sericin depleted silk fibers; (g) the yarns are made with 3 ends of Td 20/22 ra(g) w silk twisted together in the S direction to form a ply with 20 tpi and further combining 3 of the resulting ply with 10 tpi in the Z direction, and; (h) the stitch density or pick count for silk mesh design is 40 picks per centimeter including the total picks count for the technical front face and the technical back face of the mesh, or equivalently 20 picks per cm considering only one face of the mesh.

DRAWINGS

The present invention can be more fully understood from the detailed description and the accompanying drawings, which are not necessarily to scale, wherein:

FIGS. 1F and 1G illustrate an example pattern layout for a double needle bed mesh or scaffold according to aspects of the present invention from FIG. 1B for pattern bar #5.

FIGS. 1H and 1I illustrate an example pattern layout for a double needle bed mesh or scaffold according to aspects of the present invention from FIG. 1B for ground bar #7.

FIG. 1J illustrates an example pattern simulation for a double needle bed mesh demonstrated in FIG. 1B according to aspects of the present invention.

FIG. 1K shows the yarn feed rates used during the knit process used to make the most preferred embodiment of the device within the scope of the present invention.

FIG. 3A shows a scanning electromicrograph ("SEM") of native silk fibers. FIG. 3B shows a SEM of sericin extracted silk fibers useful to make the device. The size bar at the top of each of FIG. 3A and FIG. 3B measures 20 microns.

FIG. 4 is a photograph of an embodiment (a knitted silk fabric ready for implantation) of a device within the scope of the present invention (placed above a millimeter ruler).

Figures 5A, 5B:
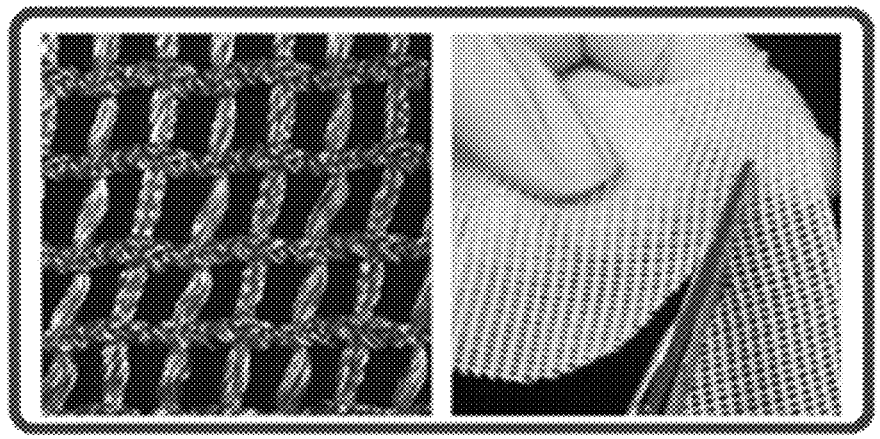

FIG. 5A is photograph at 16× magnification of a portion of the FIG. 4 embodiment.

FIG. 5B is photograph of the FIG. 4 embodiment showing the ease with which it can be cut without the fabric unraveling or fraying.

Figure 6:
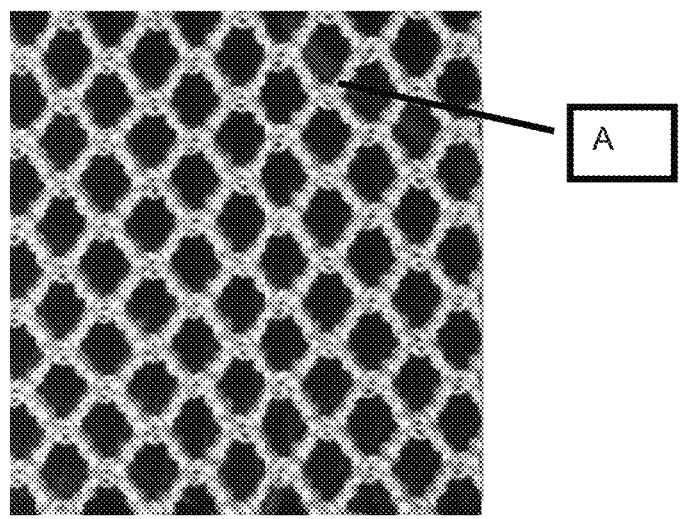

FIG. 6 is a photograph of a pattern layout for a silk-based scaffold design in accordance with the present invention ("the device" of Example 1)

Figure 7:
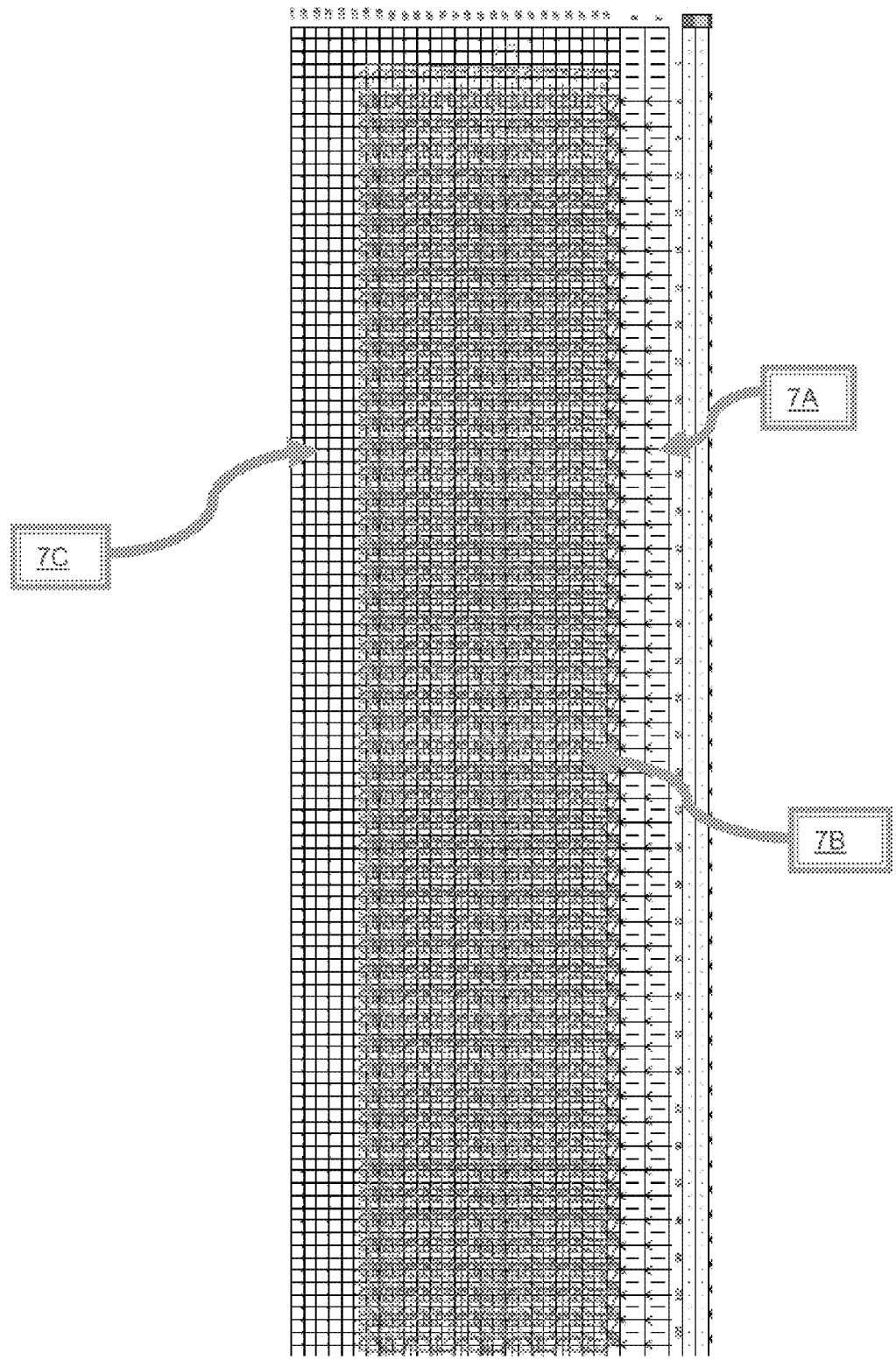

FIGS. 7 represent one of the element for the pattern layout making the device on a raschel knitting machine. 7A is the needle layout over two needle bed (front and back); 7B represent the yarn evaluation for the 4 bars making the device in FIG. 6; 7B is one of the grid equivalent to one needle space and one course (front or back of the pattern)

Figure 8:
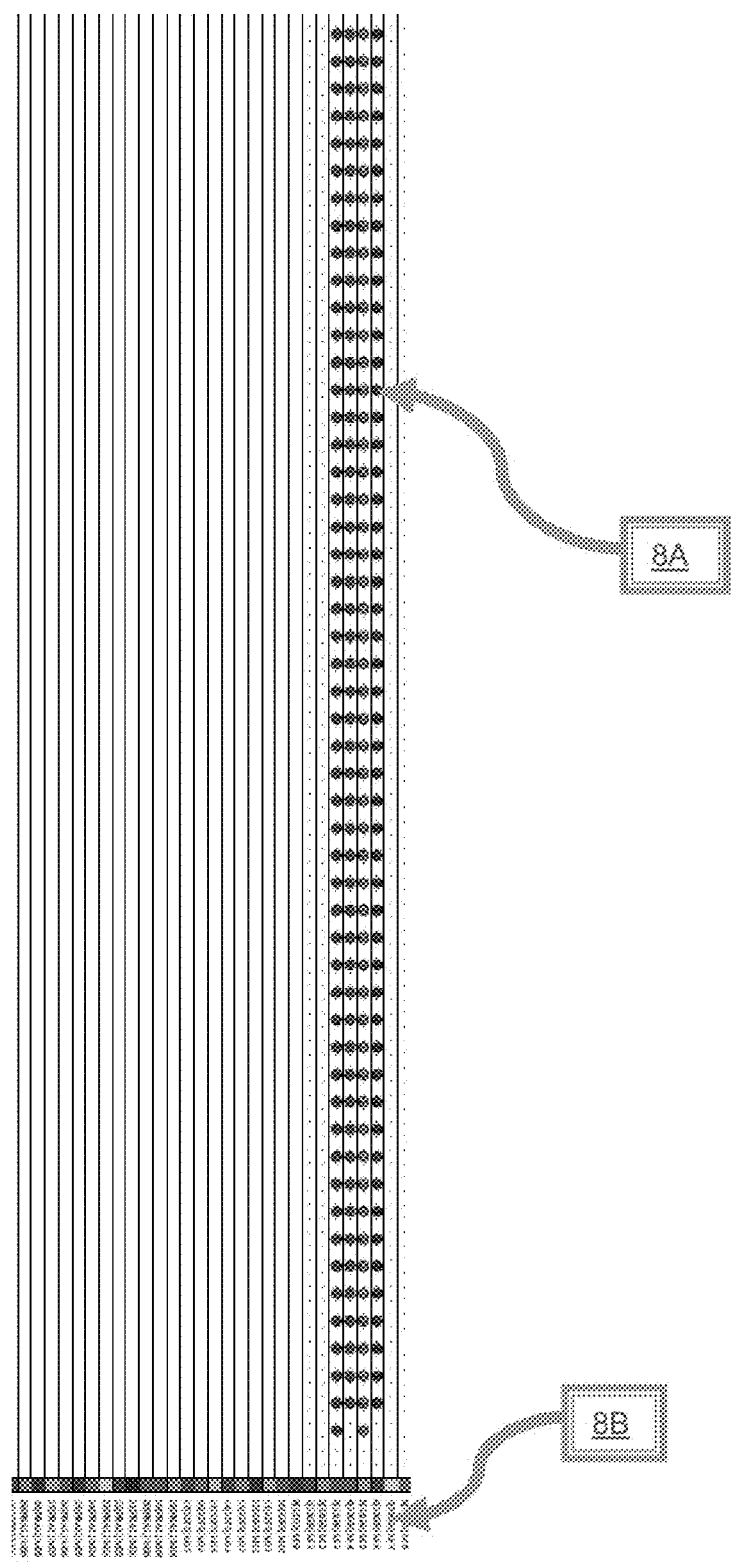

FIG. 8 represent one of the element for the pattern layout making the device on a raschel knitting machine. 8A is the threading sequence for the guide bar heddle, each color dot represent one heddle eyelet; 8B is the bar and devices numbering sequence.

Figure 9:
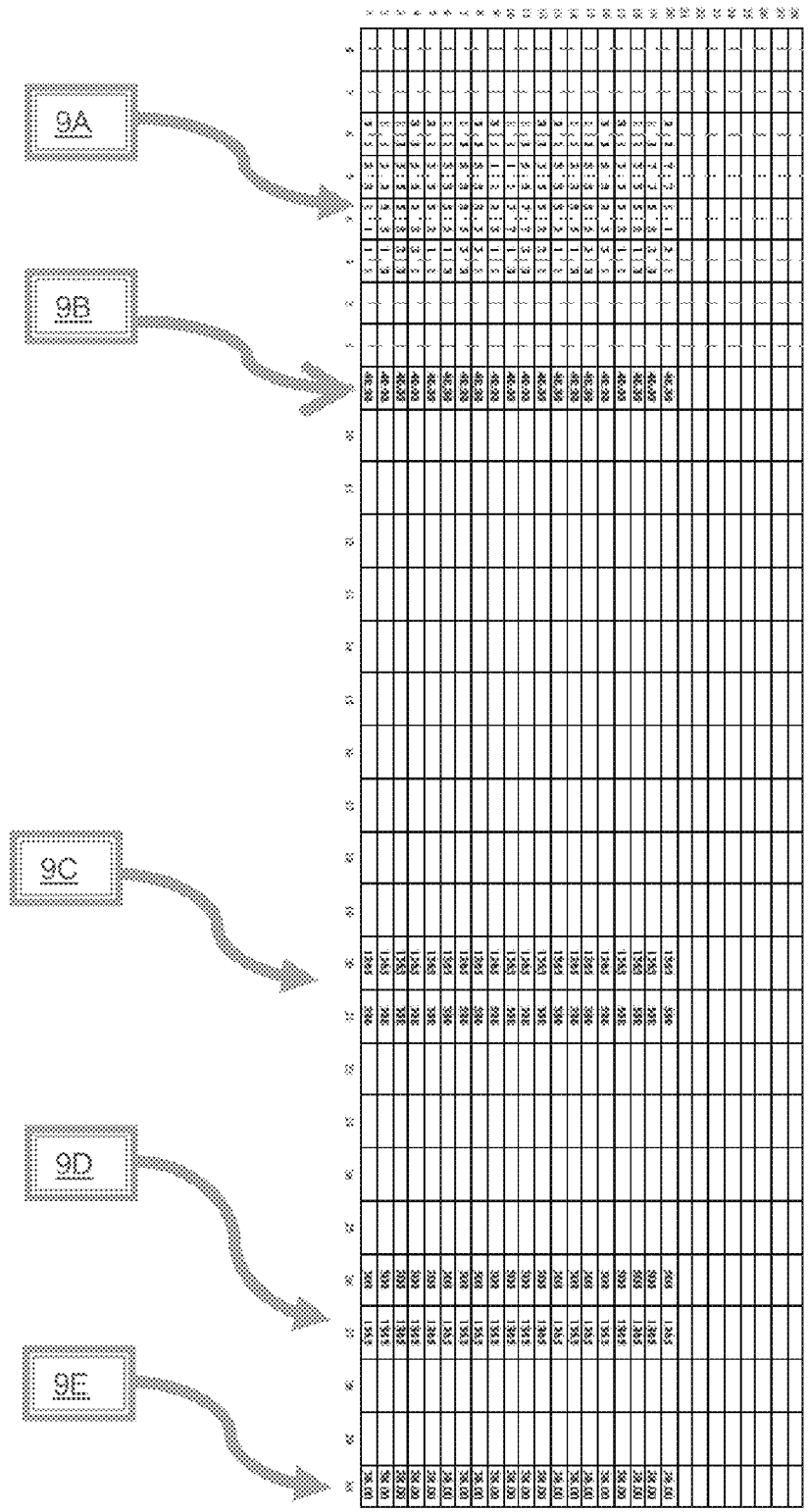

FIG. 9 represent one of the element for the pattern layout making the device on a raschel knitting machine. 9A is the sequence for the movements making up the pattern bars; 9B is the sequence for the value making up the take down; 9C-9D-9E are the sequences for the feed rate of the yarn making up the pattern. The present invention is based on discovery of an implantable, bioresorbable, biocompatible, pliable, knitted, porous silk mesh (the "device") which upon implantation provides soft tissue support and, as the device bioresorbs, transfer of its load bearing (support) function to new tissue formed at the site of implantation. The device is preferably made from Bombyx mori silkworm silk. It can also be made from spider silk, including recombinantly made spider silk. The preferred knit pattern of the device accomplishes variation in tension between yarns at the knit nodes (the yarn interlocking loops) thereby preventing unraveling of the mesh when cut for use in surgery. FIG. 5A (left hand side) shows a 16× magnification of the device knit pattern and FIG. 5B (right hand side) shows ease of cutting without fraying or unraveling.

Figure 1A:
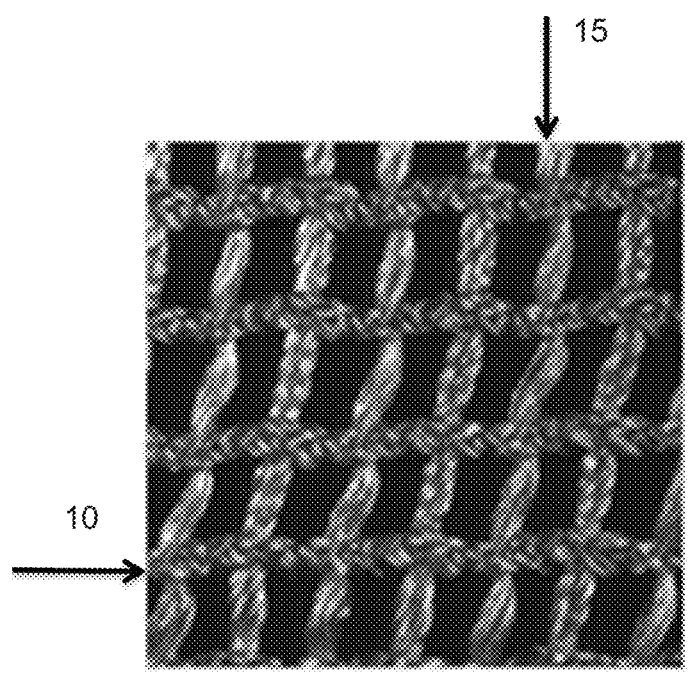
FIG. 1A is a photograph of a pattern layout for a silk-based scaffold design in accordance with the present invention.
Figure 1B:
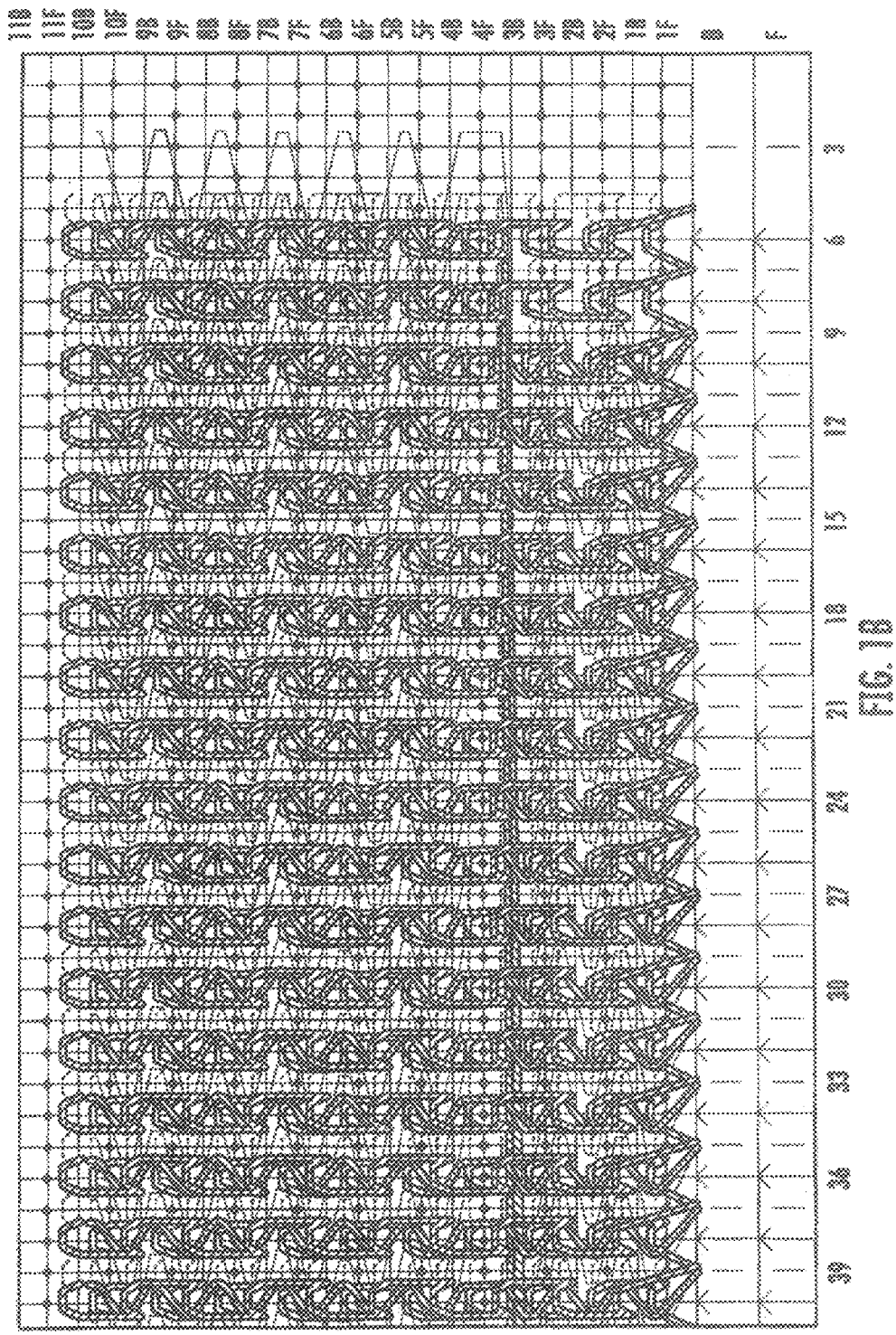
FIGS. 1B and 1C illustrate an example pattern layout for the scaffold design of FIG. 1A including all pattern and ground bars according to aspects of the present invention.
Figure 1C:
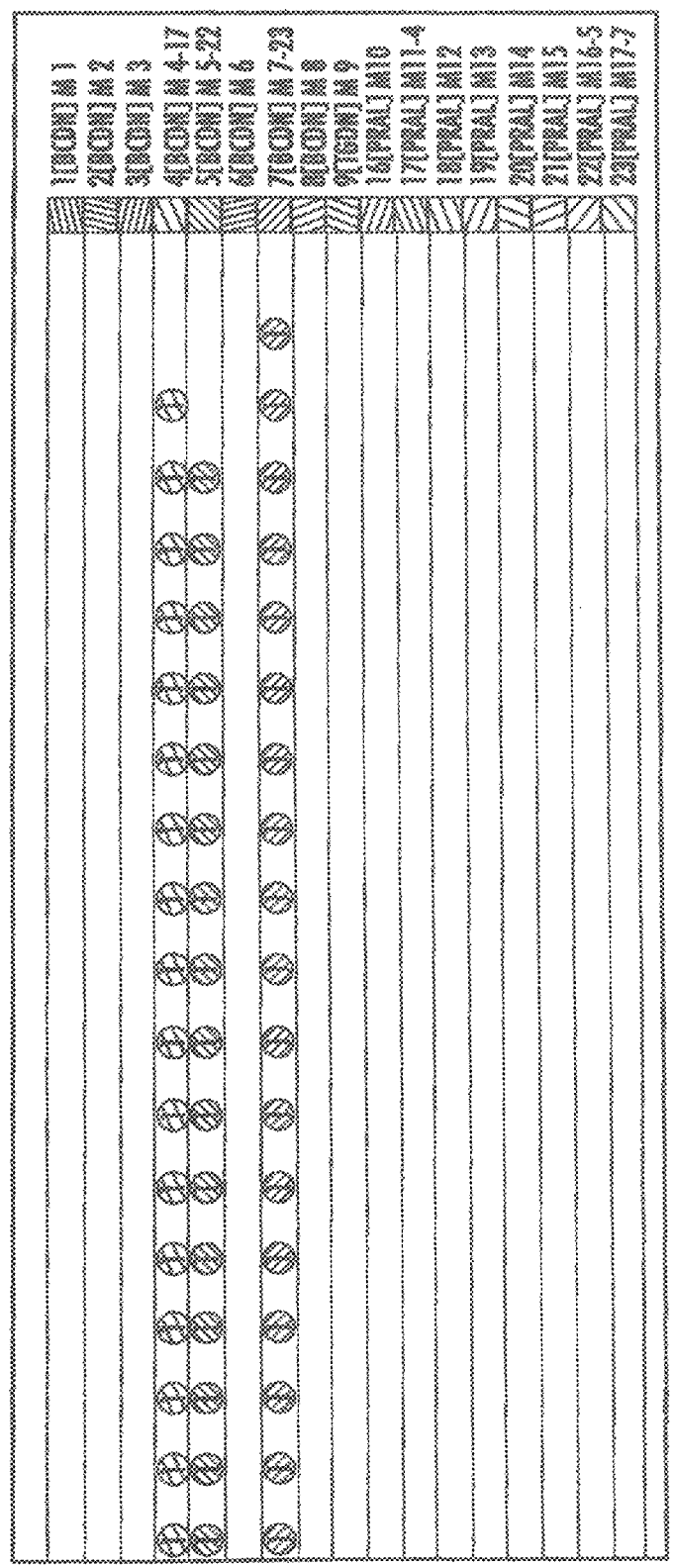

Importantly, the device made according to the present invention allows significant and consistent tissue ingrowth while bioresorbing at a rate which permits smooth transfer of load bearing support to the newly formed tissue. Thus the device is made of a biocompatible silk protein that is eventually bioresorbed. The raw silk fibers obtained from Bombyx mori silkworms comprise a fibroin protein core filament coated with the antigenic globular protein sericin. The sericin is removed or substantially all removed by hot aqueous (i.e. soap) extraction (wash) leaving behind fibroin protein filament consisting of layers of antiparallel beta sheets which provide both stiffness and toughness. FIG. 3A is a SEM photograph of native (sericin coated) silk fibers, and FIG. 3B of the fibers after sericin extraction, as then used to make (knit) the device. The porous knit structure of the device so made is shown by FIGS. 1A, 4 and 5.

Multiple sericin-depleted fibroin protein fibers are combined and twisted together to form a multi-filament yarn. The multi-filament fibroin yarn is subsequently knitted into a three dimensional pattern to serve as soft tissue support and repair. The resulting device is mechanically strong, flexible, and tear-resistant. The device is a single use only scaffold that can be produced in a variety of shapes, sizes and thicknesses and can be terminally sterilized.

The device provides immediate physical and mechanical stabilization of tissue defects because of its strength and porous construction and is useful as a transitory scaffold for soft tissue support and repair. It provides reinforcement for deficiencies where weakness or voids exist that require additional material reinforcement to obtain the desired surgical outcome. The bioresorption process occurs over time after implantation of the device as tissue in-growth and neovascularization takes place.

The device can be used to assist soft tissue repair. Examples of soft tissue repair include breast reconstruction, hernia repair, cosmetic surgery, implementation of a bladder sling, or the like.

Figure 1D:
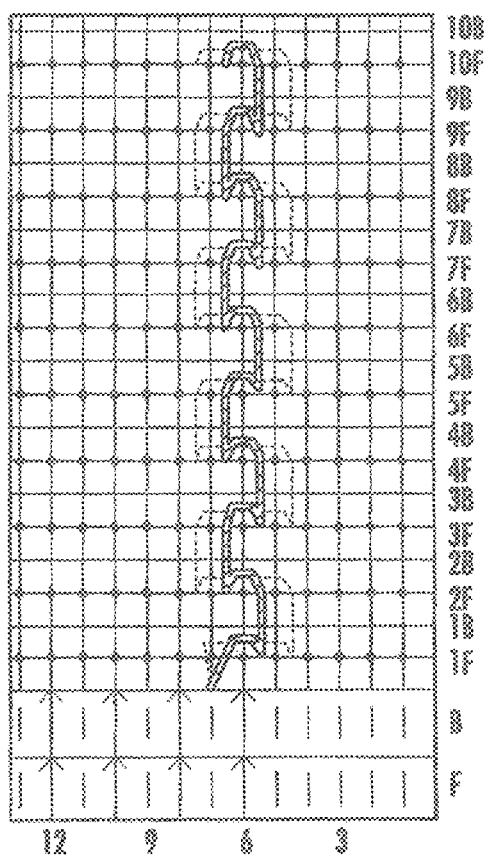
FIGS. 1D and 1E illustrate an example pattern layout for a double needle bed mesh or scaffold according to aspects of the present invention from FIG. 1B for ground bar #4.
Figure 1E:
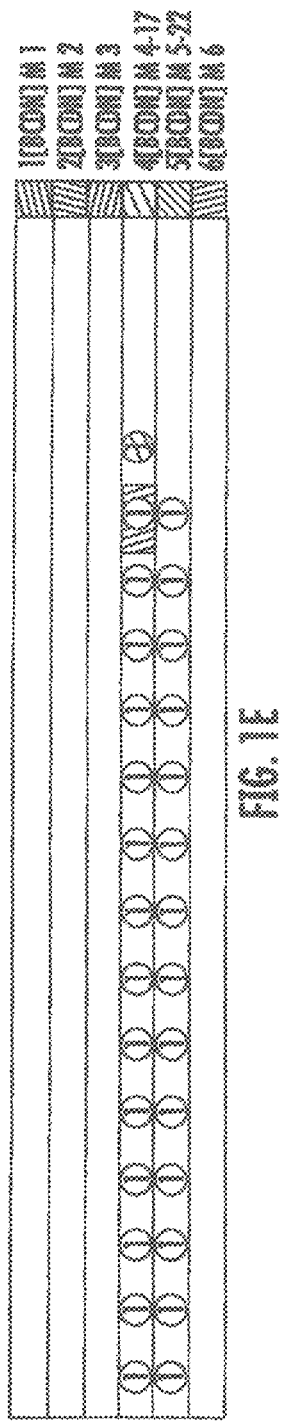
Figure 1F:
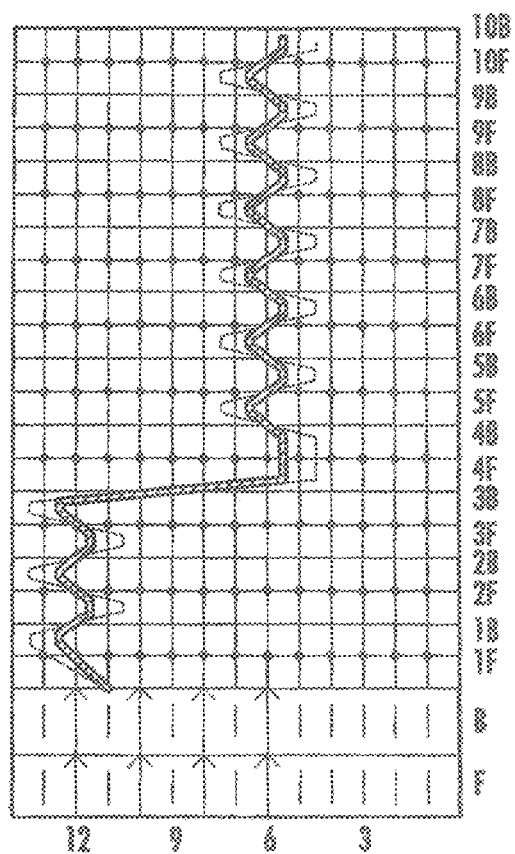
Figure 16:
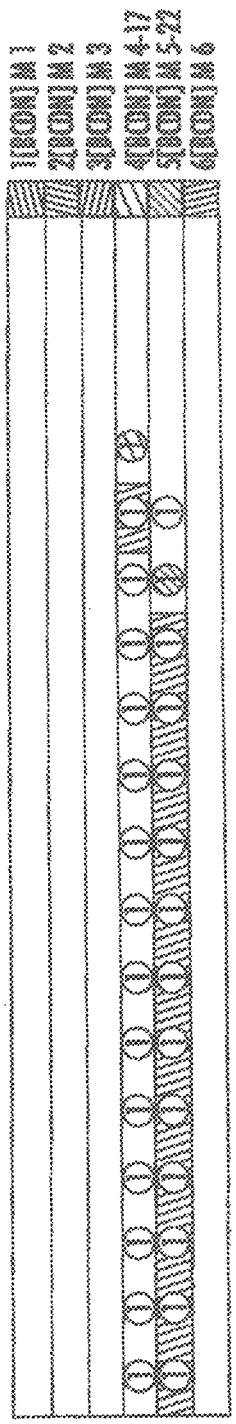
Figure 1H:
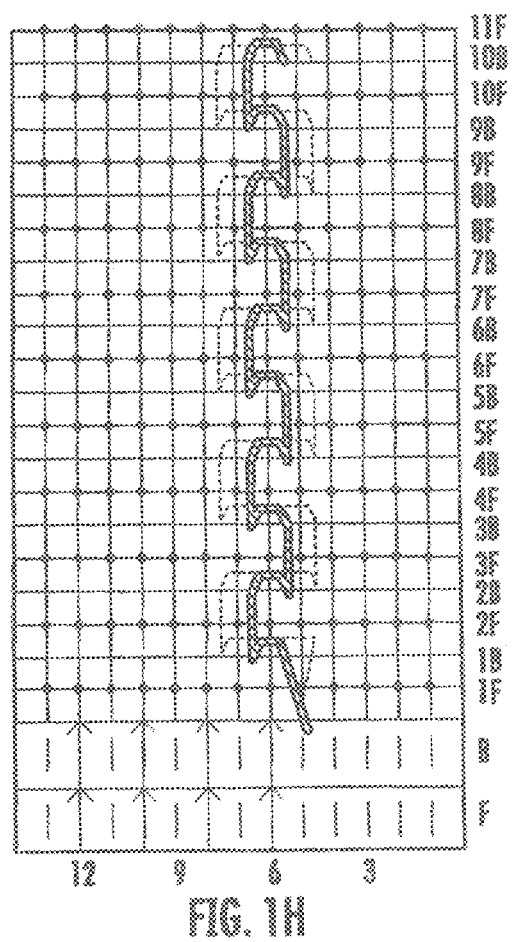
Figure 11:
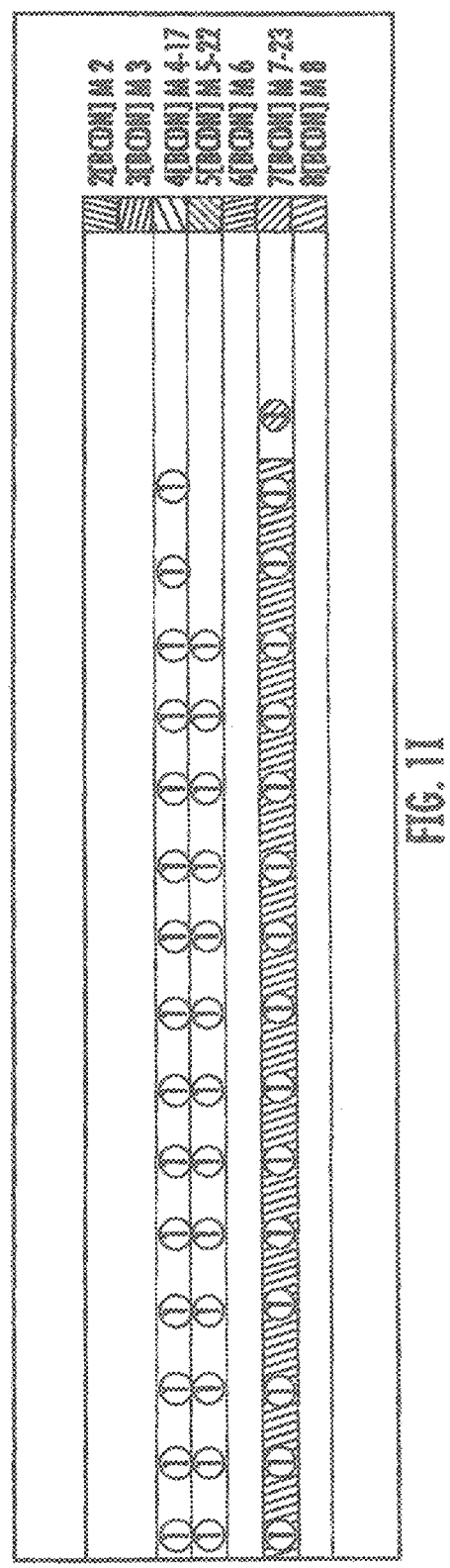
Figure 12:
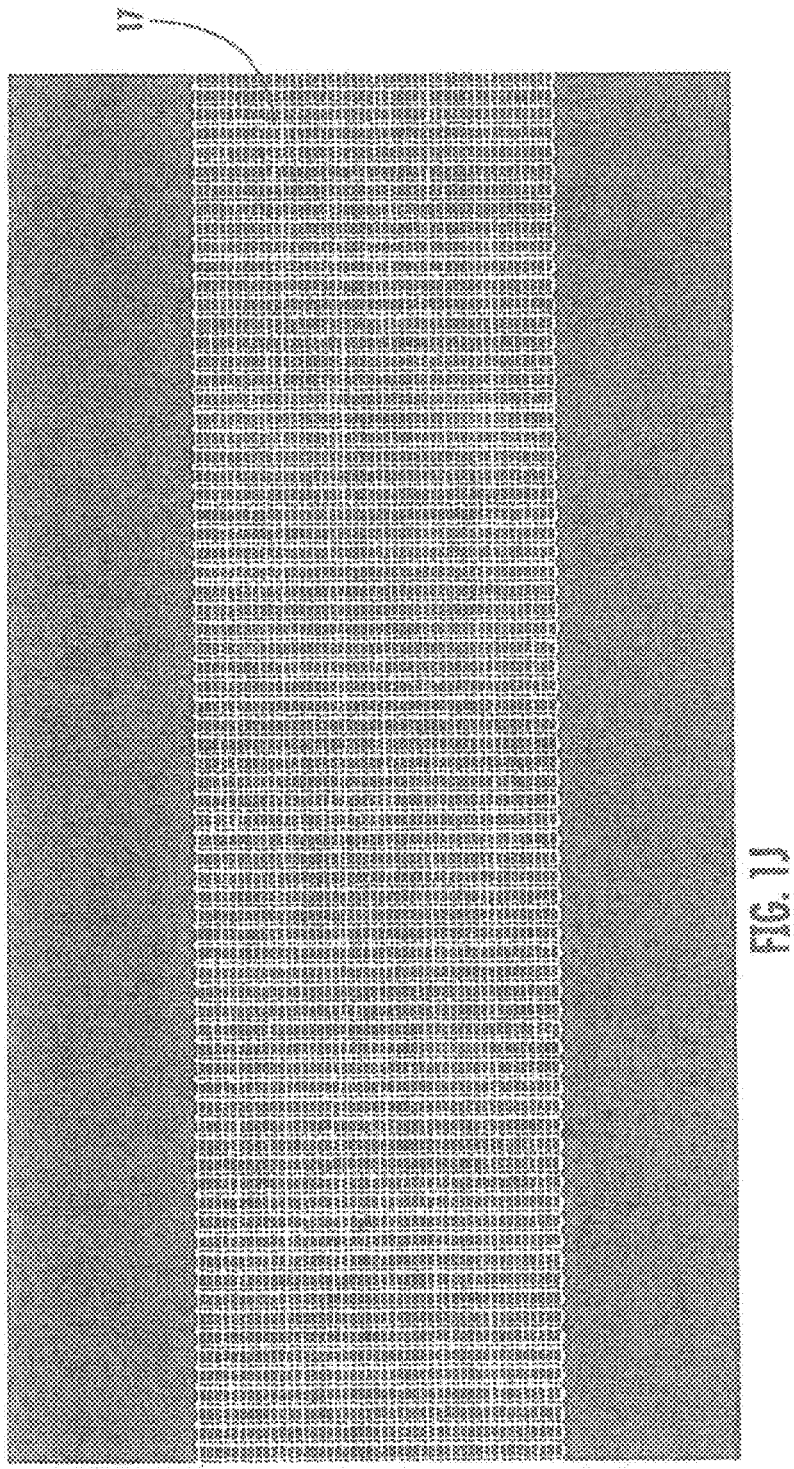
Figure 1K:
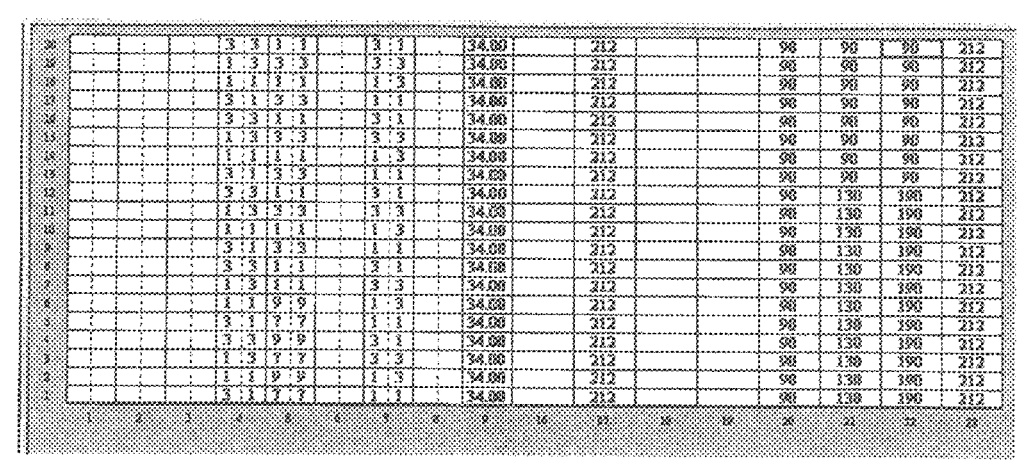

Silk is the material used to make the device. Particular embodiments may be formed from Bombyx Mori silkworm silk fibroin. As explained a preferred embodiment of the device is made using sericin extracted silk fibers with certain knit machine parameters or settings. A detailed explanation of the knit pattern and knit process used to make a most preferred embodiment of the present invention will now be set forth. FIG. 1A is a photograph of a pattern layout for a device (silk-based mesh or scaffold) in accordance with the present invention. FIG. 1A shows the wale direction 10 and the course direction 15 and placement of the silk yarns in either the wale 10 or course 15 scaffold material direction or location. The device is preferably formed on a raschel knitting machine such as Comez DNB/EL-800-8B set up in 10 gg needle spacing by the use of three movements as shown in pattern layout in FIGS. 1B and 1C: two movements in the wale direction, the vertical direction within the fabric, and one movement in the course direction, the horizontal direction of the fabric. The movements in the wale direction occur on separate needle beds with alternate yarns; loops that occur on every course are staggered within repeat. The yarn follows a repeat pattern of 3/1-1/1-1/3-3/3 for one of the wale direction movements as shown in FIGS. 1D and 1E and 1/1-1/3-3/3-3/1 for the other wale direction movement as shown in FIGS. 1H and 1I. The interlacing of the loops within the fabric allows for one yarn to become under more tension than the other under stress, locking it around the less tensioned yarn, thereby keeping the fabric from unraveling when cut. The other movement in the course direction as shown in FIG. 1F and 1G occurs in every few courses creating the porous design of the device. These yarns follow a repeat pattern of 7/7-9/9-7/7-9/9-7/7-9/9/-1/1-1/1-3/3-1/1-3/3-1/1-3/3-1/1-3/3-1/1 for the course direction movement. The pattern simulation layout of this pattern was rendered using ComezDraw 3 software in FIG. 1J considering a yarn design made with 3 ends of Td (denier count) 20/22 raw silk twisted together in the S direction to form a ply with 20 tpi (turns per inch) and further combining three of the resulting ply with 10 tpi. In FIG. 1J The same yarn design is used for the movements occurring in the wale and course directions. The stitch density or pick count for the design in FIG. 1J is 34 picks per centimeter considering the total picks count for the technical front face and the technical back face of the fabric, or 17 picks per cm considering only on the face of the fabric. The operating parameters described in FIGS. 1B to 1I are the optimum values for the specific yarn design used for the pattern simulation layout of FIG. 1J. In FIG. 1J item 17 is a simulated double needle bed mesh or scaffold. To further explain aspects shown by FIG. 1F: following standard terminology well known in the knit industry "F" means front and "B" means back and with regard to FIG. 1F shows the incremental sequence of pattern lines for the course direction. The numbers "12, 9, 6 and 3" at the bottom of FIG. 1F represent the number of needles in the needle bed starting count from left to right. The upwards pointing arrows near the bottom of FIG. 1F show the needle slots occupied by a needle actively engaged with the yarn for the knit machine/knit process. Rows 1F to 6B of FIG. 1F show the knit pattern used to make the device. The FIG. 1F rows 1F to 6B knit pattern is repeated 94 times to make a 25 cm sheet length of the fabric of the device, the number of repeats of the pattern being fewer or more if respectively a smaller or larger section of device fabric is desired to result from the knit process. The FIG. 1F rows 1F to 6B knit pattern is equivalently described by the above set forth, combined three knit movement: the first wale direction 3/1-1/1-1/3-3/3 knit pattern; the second wale direction 1/1-1/3-3/3-3/1 knit pattern, and; the course direction 7/7-9/9-7/7-9/9-7/7-9/9/-1/1-1/1-3/3-1/1-3/3-1/1 knit pattern. Rows 7F to 10B in FIG. 1F (and equivalently the terminal 3/3-1/1-3/3-1/1-3/3-1/1-3/3-1/1 portion of the course knit pattern) show the knit pattern used to make a spacer which creates a kitted area of fabric separation (i.e. a cut location) between adjacent 25 cm lengths of the knitted device fabric which is knitted by the process set forth above as one continuous sheet of fabric. The specific feed rates for the yarn forming this most preferred embodiment of the device is shown in FIG. 1 K where column 17 shows the yarn feed rate used for the first wale direction 3/1-1/1-1/3-3/3 knit pattern. A rate of 212 is equivalent to 74.8 cm of yarn per 480 coursed or per rack. Column 23 of FIG. 1K reports the yarn feed rate that is used for the second wale direction 1/1-1/3-3/3-3/1 knit pattern, where again a rate of 212 is equivalent to 74.8 cm of yarn per 480 coursed or per rack. Column 22 of FIG. 1K shows the yarn feed rate that is used for the course direction 7/7-9/9-7/7-9/9-7/7-9/9/-1/1-1/1-3/3-1/1-3/3-1/1-3/3-1/1-3/ 3-1/1-3/3-1/1-3/3-1/1 knit pattern; a rate from line 1F to 6B of 190 is equivalent to 67.0 cm of yarn per 480 coursed or per rack, while a rate from line 7F to 10B of 90 is equivalent to 31.7 cm of yarn per 480 coursed or per rack. Column 21 of FIG. 1K shows that the yarn feed rate that is used for the second to last yarn at each edge of the knitted device fabric in the course direction 7/7-9/9-7/7-9/9-7/7-9/9/-1/1-1/1-3/3-1/1-3/3-1/1-3/3-1/1-3/3-1/1-3/3-1/1 knit pattern; a rate from line 1F to 6B of 130 is equivalent to 45.8 cm of yarn per 480 coursed or per rack, while a rate from line 7F to 10B of 90 is equivalent to 31.7 cm of yarn per 480 coursed or per rack. Column 20 of FIG. 1K reports (shows) the yarn feed rate that is used for the last yarn at each edge of the knitted device fabric in the course direction 7/7-9/9-7/7-9/9-7/7-9/9/-1/1-1/1-3/3-1/1-3/3-1/1-3/3-1/1-3/3-1/1-3/3-1/1 knit pattern; a rate from line 1F to 6B of 130 is equivalent to 45.8 cm of yarn per 480 coursed or per rack, while a rate from line 7F to 10B of 90 is equivalent to 31.7 cm of yarn per 480 coursed or per rack.

The knit pattern shown in FIG. 1A can be knit to any width depending upon the knitting machine and can be knitted with any of the gauges available with the various crochet machines or warp knitting machines. Table 1 outlines the device fabric widths that may be achieved using a different numbers of needles on different gauge machines. The dimensions in Table 1 are approximate due to the shrink factor of the knitted fabric which depends on stitch design, stitch density, and yarn size used.

TABLE 1

|  | Needle Count | | Knitting Width (mm) | |
|---|---|---|---|---|
| Gauge | From | To | From | To |
| 48 | 2 | 5656 | 0.53 | 2997.68 |
| 24 | 2 | 2826 | 1.06 | 2995.56 |
| 20 | 2 | 2358 | 1.27 | 2994.66 |
| 18 | 2 | 2123 | 1.41 | 2993.43 |
| 16 | 2 | 1882 | 1.59 | 2992.38 |
| 14 | 2 | 1653 | 1.81 | 2991.93 |
| 12 | 2 | 1411 | 2.12 | 2991.32 |
| 10 | 2 | 1177 | 2.54 | 2989.58 |
| 5 | 2 | 586 | 5.08 | 2976.88 |

Figure 2:
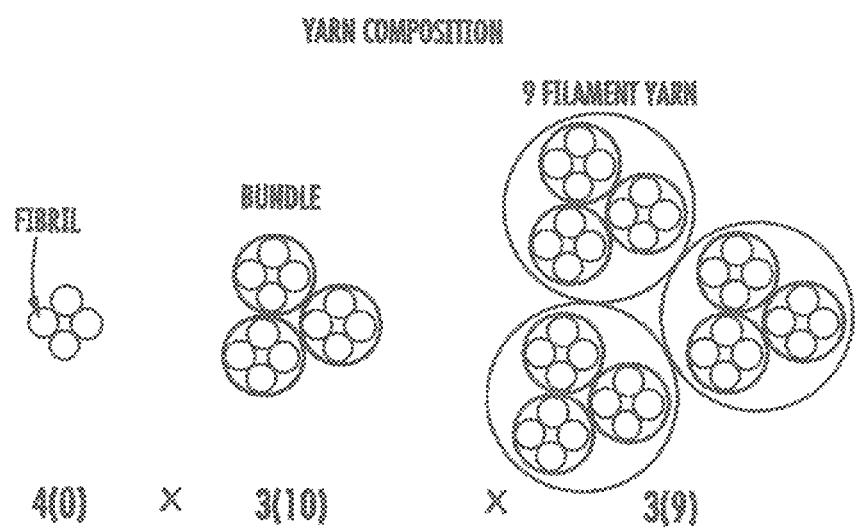
FIG. 2 illustrates the twisting and multi-ply nature of a yarn comprised of silk fibroin bundles as used in an embodiment of the present invention.

The device was knit with 9-filament, twisted silk yarns. A yarn was made from three silk bundles, each of which was comprised of individual silk fibrils as illustrated in FIG. 2. The 9-filament yarns were knit into the surgical scaffold. The wales ran horizontally and the courses ran vertically along the scaffold.

A preferred embodiment of the device ready for surgical use has a thickness between about 0.6 mm and about 1.0 mm, a width of about 10 cm (±about 1 cm) and a length of about 25 cm (±about 3 cm). Additionally the device has pores with an average diameter greater than about 10,000 um$^2$, a density of from about 0.14 mg/mm$^3$ to about 0.18 mg/mm$^3$ (as determined by dividing the mass of the device by its volume [thickness, width, and length multiplied together]), and is comprised of at least about 95% silk fibroin. Furthermore, the device has a burst strength of from about 0.54 MPa to about 1.27 MPa, and a stiffness of between about 30N/mm to about 50 N·mm (the latter two mechanical properties of the preferred device determined by American Society for Testing and Materials D3787-07, "Standard Method for Burst Strength of Textiles: Constant Rate of Transverse Ball Burst Test" or ASTM F2150-07 Standard Guide for Characterization and Testing of Biomaterial Scaffolds Used in Tissue Engineered Medical Products)

The density of the device was calculated using the equation:

$$\text{Material Density} = \frac{\text{Mass [mg]}}{(\text{Average Length [mm]}) \times (\text{Average Width [mm]}) \times (\text{Thickness [mm]})}$$

The cross-sectional area of full pores of the scaffold was measured using a microscope with sufficient magnification and image capture capability. The magnification was selected based upon the resolution of the pores in the knit pattern being examined.

Ball Burst Testing—Per ASTM D3787-07, each device tested was compressed between the two circular fixation brackets of the mechanical testing equipment, while leaving exposed a circular area of the test article that covers the radius of the inner fixture diameter. The sample device was secured with a constant fixation bolt torque to the locking nuts of the burst jig. Care was taken to ensure that the knit structure of the sample was organized and not skewed or sheared. The sample remained taut within the fixation brackets with equal distribution of tension. The ball burst fixture was attached to the mechanical testing equipment with a calibrated load cell. For the burst test, the fixture ball was inserted through the center diameter of the fixation brackets with a uniform pressure applied to the test article. The ball was inserted at a constant rate until the scaffold fails.

Burst stiffness was calculated by determining the slope of the middle 60% of the linear region of the compressive load vs. extension curve.

Maximum burst strength was calculated using the equation:

$$\text{Maximum Burst Strength } [MPa] = \left[\frac{\text{Maximum Burst Load } [N]}{\text{Exposed Area } [m^2]}\right] \times 10^{-6}$$

The exposed area was the circular area of the test article covering the radius (r) of the inner fixture diameter and was calculated using the equation below.

$$\text{Exposed Area} = \pi r^2$$

Tensile Testing—The tensile strength and elongation of the device were measured in accordance with ASTM D5035. Device samples were clamped in the mechanical test equipment. The upper clamp was mounted to the load cell, which was attached to the actuator and the lower clamp was mounted to the support plate. The lower limit of the actuator was set so that the upper and lower clamps were prevented from colliding. The upper clamp was aligned to make the faces of both clamps parallel to each other. The height of the mechanical equipment crosshead was adjusted so that the actuator was positioned to allow for a defined amount of upward movement and a specific sample gauge length resided between the upper and lower sample clamps.

The device was loaded by clamping the first 10 mm of the sample into the upper clamp and allowing the remainder of the sample to fall unrestrained into the bottom clamp opening. The last 10 mm of the sample was held by the bottom clamp. Care was taken to avoid pre-staining the device sample. Once the sample was clamped the actuator height was adjusted so that the sample had a pre-load of 2N. The actuator position was adjusted to achieve a specific gauge length and then reset to the zero-position at this point. The device sample was strained until it experienced ultimate tensile failure. The average maximum tensile strength, maximum tensile stress, percent elongation at break, and the tensile stiffness were determined. Tensile stiffness was calculated by determining the slope of the trend line of the linear portion of the tensile load vs. elongation curve bound by an upper and lower tensile load.

Tensile stiffness was calculated as the slope of the linear portion of the load verses elongation curve. The average maximum tensile strength, maximum tensile stress, linear stiffness, and percent elongation at break were determined.

Maximum tensile stress was calculated using the equation:

$$\text{Maximum Tensile Stress } [MPa] = \left[\frac{\text{Maximum Tensile Strength } [N]}{\text{Width } [m] \times \text{Thickness } [m]}\right] \times 10^{-6}$$

Whereby, the thickness and width were provided by the respective device sample thickness and width measurements.

Percent elongation at break was determined using the equation:

$$PercentElongationatBreak[\%] = \left[\frac{\text{Elongation at Break } [mm]}{\text{Length } [mm]}\right]\%$$

Whereby, length was provided by the respective device sample length measurement.

Tear testing—A device sample with a width that is two-thirds that of the length was cut from each device. Before the samples are incubated in phosphate buffered saline, a small cut that was one-fourth the size of the sample width was made in the center of the device sample perpendicular to the length (through a single row of wales). Mechanical test equipment was used to measure the maximum tear resistance load. Clamps were inserted in the equipment. The upper clamp was mounted to the load cell that was attached to the actuator and the lower clamp was mounted to the base support plate. The lower limit of the actuator was set so that the upper and lower clamps were prevented from colliding. The upper clamp was aligned to make the faces of both clamps parallel to each other. The height of the mechanical equipment crosshead was adjusted so that the actuator was positioned to allow for a defined amount of upward movement and a specific sample gauge length resided between the upper and lower clamps. The device sample was placed in the upper clamp. The top 10 mm of the sample was covered by the clamp. The device sample was positioned so that the cut was located on the left side. The sample was aligned perpendicular with the clamp before the clamp was closed. The bottom portion of the sample was allowed to fall unrestrained into the bottom clamp opening. The clamp was closed and the sample was preloaded with 3N. The sample was strained at a constant rate until the sample tore at the cut point. From the resulting data the maximum tear resistance load was obtained.

Embodiments of the device according to the present invention can be knitted on a fine gauge crochet knitting machine. A non-limiting list of crochet machines capable of manufacturing the surgical mesh according to aspects of the present invention are provided by: Changde Textile Machinery Co., Ltd.; Comez; China Textile Machinery Co., Ltd.; Huibang Machine; Jakkob Muller AG; Jingwei Textile Machinery Co., Ltd.; Zhejiang Jingyi Textile Machinery Co., Ltd.; Dongguan Kyang the Delicate Machine Co., Ltd.; Karl Mayer; Sanfang Machine; Sino Techfull; Suzhou Huilong Textile Machinary Co., Ltd.; Taiwan Giu Chun Ind. Co., Ltd.; Zhangjiagang Victor Textile; Liba; Lucas; Muller Frick; and Texma.

Embodiments of the device according to the present invention can be knitted on a fine gauge warp knitting machine. A non-limiting list of warp knitting machines capable of manufacturing the surgical mesh according to aspects of the present invention are provided by: Gomez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Embodiments of the device according to the present invention can be knitted on a fine gauge flat bed knitting machine. A non-limiting list of flat bed machines capable of manufacturing the surgical mesh according to aspects of the present invention are provided by: Around Star; Boosan; Cixing Textile Machine; Fengshen; Flying Tiger Machinary; Fujian Hongqi; G & P; Gorteks; Jinlong; JP; Jy Leh; Kauo Heng Co., Ltd.; Matsuya; Nan Sing Machinery Limited; Nantong Sansi Instrument; Shima Seiki; Nantong Tianyuan; and Ningbo Yuren Knitting.

A test method was developed to check the cutability of the device formed according to aspects of the present invention. In the test method the device evaluated according to the number of scissor strokes needed to cut the device with surgical scissors. The mesh was found to cut excellently because it took only one scissor stroke to cut through it. The device was also cut diagonally and in circular patterns determining that the device did not unraveled once cut in either or both its length and width directions (see FIG. 5B). To determine further if the device would unravel a suture was passed through the closest pore from the cut edge, and pulled. This manipulation did not unravel the device. Thus the device was easy to cut and did not unravel after manipulation.

A device according to the present invention has been found to bioresorb by 50% in approximately 100 days after implantation, that is at least about 50% of the mass of the device bioresorbs after about 100 days after implantation in a human patient.

Physical properties of the device include thickness, density and pore sizes. The thickness of the device was measured utilizing a J100 Kafer Dial Thickness Gauge. A Mitutoyo Digimatic Caliper was used to find the length and width of the samples; used to calculate the density of the device. The density was found by multiplying the length, width and thickness of the mesh then dividing the resulting value by the mass. The pore size of the device was found by photographing the mesh with an Olympus SZX7 Dissection Microscope under 0.8× magnification. The measurements were taken using ImagePro 5.1 software and the values were averaged over several measurements. Physical characteristics of sample meshes, and two embodiments of the device are shown in Table 2.

TABLE 2

| Sample | Physical Characterization | | |
|---|---|---|---|
| | Thickness (mm) | Pore Size (mm$^2$) | Density (g/cm$^3$) |
| Mersilene Mesh | 0.31 ± 0.01 | 0.506 ± 0.035 | 0.143 ± 0.003 |
| Bard Mesh | 0.72 ± 0.00 | 0.465 ± 0.029 | 0.130 ± 0.005 |
| Vicryl Knitted Mesh | 0.22 ± 0.01 | 0.064 ± 0.017 | 0.253 ± 0.014 |
| Device knit on a single needle bed machine | 1.00 ± 0.04 | 0.640 ± 0.409 | 0.176 ± 0.002 |
| Device knit on a double needle bed machine | 0.89 ± 0.003 | 1.26 ± 0.400 | ±0.005 |

EXAMPLE 1

Pliable Silk Medical Device

We developed a pliable silk medical device ("the device" in Examples 1-6) and methods for making the device. By pliable it is meant that the device can stretched to increase its length and/or its width by between about 4% to about 110% before breaking (see Table 5 below). The device is a pliable, knitted, biocompatible silk scaffold device that can be implanted in a surgical procedure to provide soft tissue repair and soft tissue support, including to support an implant such as a breast implant or a tissue expander. Examples of soft tissue repair surgical procedures include breast reconstruction, hernia repair, cosmetic surgery, and implementation of a bladder sling. Although the device can employ a variety of polymer materials, preferable the device is made of silk, such as *Bombyx Mori* silkworm silk fibroin. The raw silk fibers used to make the device have a natural globular protein coating known as sericin, which may have antigenic properties and must be depleted before implantation of the device. Accordingly, yarn used to make the device is taken through a sericin depletion process as described in Altman et al., "Silk matrix for tissue engineered anterior cruciate ligaments," Biomaterials 23 (2002), pp. 4131-4141, the contents of which are incorporated herein by reference in its entirety. After the depletion process the silk material used in the device embodiments contains substantially no sensitizing agents.

The device is preferably made by knitting sericin depleted silk yarn to form a porous mesh or fabric. The knitting can be carried out as raschel knitting, warp knitting and weft knitting. After being knitted the fabric of the device can be treated to enhance one or more device characteristics. The device treatment can be a finishing or surface coating process which can increase device hydrophilicity, biocompatibility and mechanical properties, such as handling for ease of cutting and graft pull-through, as well as add an anti-microbial or anti-fungal coatings. Specific examples of device surface treatments can include:

plasma modification
protein such as but not limited to fibronectin, denatured collagen or gelatin, collagen gels and
hydrophobic by covalent link or other chemical or physical method
peptides with hydrophilic and a hydrophobic end
peptides contain one silk-binding sequence and one biologically active\
sequence
biodegradable cellulose
surface sulfonation
ozone gas treatment
physically bound and chemically stabilized peptides
DNA/RNA aptamers
Peptide Nucleic Acids
Avimers
modified and unmodified polysaccharide coatings
carbohydrate coating
anti-microbial coatings
anti-fungal coatings phosphorylcholine coatings As shown in Table 3 devices of varying width were made using different numbers of needles (needle count) on different gauge knitting machines. The device can be knit to any width limited by the knitting machine width and could be knitted with any of the gauges available with the various warp knitting machine.

TABLE 3

| Gauge | Needle Count | Knitting Width (mm) |
|---|---|---|
| 48 | 2-5,656 | 0.53-2,997.68 |
| 24 | 2-2,826 | 1.06-2,995.56 |
| 20 | 2-2,358 | 1.27-2,994.66 |

TABLE 3-continued

| Gauge | Needle Count | Knitting Width (mm) |
|---|---|---|
| 18 | 2-2,123 | 1.41-2,993.43 |
| 16 | 2-1,882 | 1.59-2,992.38 |
| 14 | 2-1,653 | 1.81-2,991.93 |
| 12 | 2-1,411 | 2.12-2,991.32 |
| 10 | 2-1,177 | 2.54-2,989.58 |
| 5 | 2-586 | 5.08-2,976.88 |

Embodiments of a prosthetic device according to our invention can be knitted on a fine gauge warp knitting machine. The following is a list of warp knitting machines capable of manufacturing the device: Gomez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Embodiments of the device were knitted on a COMEZ DNB/EL-800-8B/P—20 warp knitting machine in 20 gauge with stroke for each of the positions from 1 through 30 as shown in Table 4.

TABLE 4

| Position | Maximum stroke (mm) per pattern line |
|---|---|
| 1-8 | 1.25-60.00 |
| 9 | 0.33-1.00 |
| 11-29 | 0.01-38.65 |
| 30 | 0.33-1.00 |

Our device has deformation properties that can be controlled by varying parameters within the device design, as set forth below to achieve desired device deformation ("i.e. pliable") properties. A preferred and desired deformation property is the ability of the knitted device to exhibit at least about a 30-35% extension of its length in the machine direction and at least about 25-30% extension of its length in the cross direction without breaking or unraveling. These device properties are desired because they provide stretch or pliability for the physician user at the time of device implantation, therefore permitting the user to alter the device dimensions at the time of device implantation.

FIG. 6 is a photograph of an embodiment of a pattern layout for the device, showing a silk-based scaffold design. In FIG. 6 item A is a hexagonal or diamond shaped pore device each with a square area of about 4 square millimeters, other shape configuration may be designed such as round or polygonal as well as a different square area value. This device is preferably created on a raschel knitting machine such as Gomez DNB/EL-800-8B-P set up in 10 gg needle spacing by the use of four movements as shown by the pattern layout in FIG. 7 and FIG. 8 and FIG. 9 with two movements in the wale direction, the vertical direction within the fabric, and two movements in the course direction, the horizontal direction of the fabric.

The movements in the wale direction occur on separate needle beds with alternate yarns; loops that occur on every course are staggered within repeat. While being knit the yarn follows a repeat pattern of 3/1-1/1-1/3-3/3 for one of the wale direction movements and 1/1-1/3-3/3-3/1 for the other wale direction movement, with each number representing a position, each "I" representing a guide bar movement, and each "-" representing a course (or stitch). For example, a yarn following a pattern of 3/1-1/1-1/3-3/3 would start in position 3 (located between the second and third needle slots) and move, as indicated by the "/", to position 1. The knitting needles would form a stitch (as indicated by the "-"), remain in position 1 (since 1/1 represents no movement), form another stitch, move from position 1 to position 3, form another stitch, and then remain in position 3 (since 3/3 would also represent no movement). The pattern would repeat for the full length of the fabric. The same notation method can be applied to all stitch patterns and on all guide bars listed.

The interlacing of the loops within the fabric of the device as it is being knit allow for one yarn to be under more tension than the other under stress, locking it around the less tensioned yarn; keeping the fabric from unraveling when cut. One of the other two movements in the course direction occurs in every few courses creating the porous design of the scaffold. As being knit these yarns follow a repeat pattern of 3/3-3/3-5/5-5/5-3/3-3/3-5/5-5/5-1/1-1/1-5/5-5/5-3/3-3/3-5/5-5/5-3/3-3/3-7/7-7/7 for the course direction movement. The other movements in the course direction occur in every few courses creating the openings in the scaffold. These yarns follow a repeat pattern of 1/1-5/5-5/5-3/3-3/3-5/5-5/5-3/3-3/3-7/7-7/7-3/3-3/3-5/5-5/5-3/3-3/3-5/5-5/5-1/1 for the course direction movement. The pattern adopts a yarn design made with 3 ends of Td 20/22 raw silk twisted together in the S direction to form a ply with 20 tpi and further combining 3 of the resulting ply with 10 tpi in the Z direction. The same yarn design is used for the movements occurring in the wale and course directions. The stitch density or pick count for the scaffold design is preferably 40 picks per centimeter including the total picks count for the technical front face and the technical back face of the fabric, or equivalently 20 picks per cm considering only one face of the fabric. The operating parameters are not limited to those described but just the optimum values for the physical properties of the device as a mesh or scaffold with the knit structure set forth which includes a twisted yarn. Sericin is preferably removed from the silk fibroin fibers after the yarn is formed (that is after the silk fibroin fibers have been twisted together, but not yet knitted) but before the mesh has been knit and/or after the device has been knitted. A preferred embodiment of the device is made of a 9 filament, twisted, and purified (sericin depleted) silk fiber. Once so formed into yarn (made from the twisted silk fibroin fibers) the yarn is then warp knitted as set forth above to thereby make the device. The properties of the device (mesh) include improved drapability, stretch, and conformability as compared to SERI standard 102 (SERI Surgical Scaffold), as shown in Table 5 below, where "SERI Standard 102" is the known SERI® Surgical Scaffold, and "SERI Pliable Sterilized" is the present device.

TABLE 5

| Test Parameter | SERI Standard 102 | SERI Pliable Sterilized |
|---|---|---|
| Burst Stiffness (N/mm) | 41[1] | 25[3] |
| % Elongation @ break- FF | 51[1] | 109[2] |
| % Elongation @ break- FW | 33[1] | 81.36[2] |
| % Elongation @ 16N- FF | 6.8[2] | 33.3[2] |
| % Elongation @ 16N- FW | 3.9[2] | 32.1[2] |

[1] n = 4 devices average
[2] n = 20 devices average
[3] n = 15 devices average

The Table 5 properties were achieved, in part, by creating a symmetrical, diamond shaped pore that allows for bidirectional stretch. Selected further physical properties of an embodiment of the device are shown by Table 6.

TABLE 6

| Test Parameter | Mean |
| --- | --- |
| Burst Strength (MPa) | 0.45[1] |
| Stiffness (N/mm) | 25.65[2] |
| Tensile Stress- FF | 6.61[1] |
| % elongation @ break- FF | 109.26[1] |
| Tensile Stress- FW | 2.86[1] |
| % elongation @ break- FW | 81.36[1] |
| Tear Strength (N)- FF | 148.86[1] |
| Tear Strength (N)- FW | 83.72[1] |
| SPO force N/suture FF | 16.98[1] |
| SPO force N/suture FW | 19.57[1] |
| % Elongation @ 16N- FF | 33.32[1] |
| % Elongation @ 32N- FF | 44.44[1] |
| % Elongation @ 16N- FF | 32.17[1] |
| % Elongation @ 32N- FF | 41.95[1] |
| Density (mg/mm) | 0.13[1] |

[1] n = 20 devices
[2] n = 15 devices
Table Legend
MPa means Mega Pascal
N/mm means Newton per millimeter
FF means fabric formation (fabric length)
FW means fabric width
N means Newton
mg/mm means milligram per millimeter.

EXAMPLE 2

Use of Pliable Silk Device in Two Stage Breast Reconstruction

The pliable silk device of Example 1 ("the device") can be used as a transitory scaffold for soft tissue support and repair in two-stage breast reconstruction to reinforce deficiencies where weakness or voids existed that required the addition of material to obtain the desired surgical outcome. The device is supplied sterile in a with one device utilized per breast. The device placed during each subject's stage I breast reconstruction with a tissue expander placement procedure. Following mastectomy (either immediate or delayed), the surgical site is readied for subpectoral tissue expander insertion in accordance with standard surgical methods. The tissue expander is rinsed in antibiotic solution (according to standard of care) and inserted into the subpectoral pocket. The device s cut to size (prior to, during, and/or after suturing) to repair the void between the pectoral muscle and the chest wall (i.e., inframammary fold region). The device is rinsed with antibiotic solution and sutured in place, with a minimum suture bite of 3 mm or one full row of material. If any cutting is performed in situ, rinsing of the implant site is performed. Intra-operative photography is taken of the device prior to closure. The tissue expander is filled as appropriate, drains placed according to usual standard of care and number and location of drain(s) noted. Standard rinsing of the surgical site and closure is performed. Prophylactic antibiotic use and duration is documented.

In a second surgical procedure, the tissue expander is removed and replaced with a breast implant. The surgical approach used to remove the tissue expander. Implant placement is subpectoralis muscle and the pocket is prepared. The breast implant is rinsed in antibiotic solution and positioned within the pocket. Closure is performed.

The device provides soft tissue support and facilitates positioning of the implanted tissue expander. The stage I implanted expander is a temporary implant. The stage II breast implant is intended to be a permanent implant, typically remaining implanted in the patient for ten or more years. The device also provides stabilization of the pectoralis muscle and can as well assist with maintenance of the position and appearance of the inframammary fold during stage I of a breast reconstruction and can provide this function after stage I as well. At the time of stage II (when the tissue expander is removed and the breast implant is implanted) the device is then fully or at least partially integrated within the underlying soft tissue which has grown into and around the pores of the scaffold. The device begins to be bioresorbed as soon as the device had been implanted in a patient and the device is completely bioresorbed after about one to four years after implantation. The device is implanted at stage I to help hold the tissue expander in place (the device is sutured in to form a pocket in which the tissue expander rests and/or the device is draped over the tissue expander). At the time of stage II when the tissue expander is removed and replaced by a breast implant (saline or gel filled) the device is not removed and the device remains in place within the patient.

Preferably, no additional or further device is implanted in the patient at stage II or thereafter. Importantly, the device implanted in the patient in stage I provides soft tissue support and along with the implanted tissue expander maintains the existence of a pocket or space during stage I (the tissue expansion stage) that is until the stage II breast implant implantation in the patient into the pocket or space so maintained during stage I. Thus the device assists to ensure that a pocket or space is available for the placement of the stage II breast implant. Significantly, the stage I implanted device is left in place implanted in the patient and is not removed. By stage II the device has be incorporated into the underlying soft tissue and vasculature has grown in and around it.

Preferably the scaffold is comprised entirely of or consists essentially of sericin depleted, knitted silkworm silk. The implanted device begins to be biodegraded or bioresorbed as soon as it is implanted in a patient. The fabric is completely (100%) bioresorbed (biodegraded) within about one year to about four years after implantation in a patient.

EXAMPLE 3

Use of Pliable Silk Device in Single Stage Breast Reconstruction

The device of Example 1 is supplied sterile in a single-use size with one device utilized per breast. The device is implanted in the subject immediately post mastectomy, during the breast implant placement surgery, in a direct-to-implant breast reconstruction procedure. In this Example the device is used in in DTI breast reconstruction is used.

Following mastectomy, the surgical site is readied for subpectoral breast implant insertion in accordance with standard surgical methods. The breast implant is rinsed in antibiotic solution and inserted into the subpectoral pocket. The device is optionally cut to size (prior to, during, and/or after suturing) to repair the void between the pectoral muscle and the chest wall (i.e., inframammary fold region). The device is rinsed with antibiotic solution and sutured in place to both the pectoralis muscle and chest wall, with a minimum suture bite of 3 mm or one full row of material. If any cutting was performed in situ, rinsing of the implant site is performed. Drains are placed according to usual standard of care and number and location of drain(s) noted. Rinsing of the surgical site with antibiotic solution and closure is performed. The surgical drain(s) is removed when deemed appropriate. The result is that the patient has breasts properly positioned and proportioned which look and feel like normal breasts. The same or a very similar procedure can be used for breast augmentation using the device.

EXAMPLE 4

General Surgical Procedures for use of the Device

The device can be used as a transitory scaffold for soft tissue support and repair to reinforce deficiencies where weakness or voids exist that require the addition of material to obtain the desired surgical outcome, including but not limited to reinforcement of soft tissues in reconstructive and plastic surgery to obtain the desired aesthetic outcome. The device should not be used in patients with a known allergy to silk nor in direct contact with bowel or viscera where formation of adhesions may occur. To use the device:

1. irrigate and aspirate the device implant site with saline following the in situ cutting of the device to remove any device particulate debris that may have been generated.
2. the device is stored in its original sealed package away from direct sources of heat at ambient room temperature.
3. handle the device using aseptic technique and sterile talc-free gloves.
4. remove the device from the package. Although the device does not require rehydration for mechanical or physical performance, a brief incubation (minimum 2-3 seconds) in sterile rinse solution is recommended prior to implantation.
5. use the type of suture or fixation system that is appropriate for the patient use.
6. sutures should be placed at least 3 mm, or one full row, from the cut edge of the device.
7. If preferred, the uncut device can be sutured over the patient defect and trimmed once secured in place followed by rinsing and aspiration.
8. the device should be sufficiently anchored to stabilize it during tissue ingrowth.
9. for laparoscopic procedures the device should be rolled along its long axis and may be delivered through a 7/8 mm or larger cannula.

EXAMPLE 5

Use of the Pliable Silk Device for Hernia Repair

In general, there are two main types of hernia repair: open hernia repair and minimally invasive (laparoscopic) repair. Open repair is a traditional hernia repair procedure. There are numerous and varied approaches for performing this type of hernia repair. Such approaches are performed routinely with local and intravenous sedation. Due to the larger size of the incision, open hernia repair is generally painful with a relatively long recovery period. Minimally invasive (laparoscopic) repair is usually performed under general anesthesia. Spinal anesthesia and local anesthesia are used under certain circumstances. Benefits associated with minimally invasive (laparoscopic) repair include shorter operative time, less pain, and a shorter recovery period.

In laparoscopic hernia surgery, a telescope attached to a camera is inserted through a small incision that is made under the patient's belly button. Two other small cuts are made in the lower abdomen. The hernia defect is reinforced with a mesh and secured in position. The device is secured in position by stitches, staples, tacks, and glue.

Another form of laparoscopic hernia repair is ventral hernia repair (laparoscopic). Incisional, ventral, epigastric, or umbilical hernias are defects of the anterior abdominal wall and may be congenital (umbilical hernia) or acquired (incisional). Incisional hernias form after surgery through the incision site or previous drain sites, or laparoscopic trocar insertion sites. Incisional hernias often occur after open surgical procedures. These hernias present with a bulge near or at a previous incision. The device (a prosthetic mesh) is used in order to minimize tension on the repair so as to reduce the chance of hernia recurrence. Traditionally, an old incision scar is incised and removed. Inspection of the entire length of the incision generally uncovers multiple hernia defects. The area requiring coverage is usually large and requires much surgical dissection. The device is used to cover the defect before closure of the wound. This is a major and often complex surgical procedure. The use of the device decreases possible recurrence. A patient typically returns to normal activity within a matter of weeks. The principles governing a laparoscopic ventral hernia repair are based on those of open Stoppa ventral hernia repair. A large piece of the device is placed under the hernia defect with a wide margin of mesh outside the defect, and the mesh is anchored in to place and secured to the anterior abdominal wall. The device is anchored into place, for example, by sutures. The device is secured to the anterior abdominal wall, for example, by tacks which are placed laparoscopically.

EXAMPLE 6

Use of the Pliable Silk Device in Abdominoplasty

The device can be used in body aesthetics and body contouring surgical procedures. One such embodiment relates to use of the device in abdominoplasty. There are various surgical procedures for performing an abdominoplasty depending upon the type of abdominoplasty to be performed. The time needed for conducting an abdominoplasty also varies depending upon the type of abdominoplasty to be performed. For example, a complete abdominoplasty typically is completed in 1 to 5 hours. A partial abdominoplasty, also referred to as a mini-tuck abdominoplasty, is typically completed in 1 to 2 hours. Following an abdominoplasty surgical procedure, reconstruction of the umbilicus, commonly referred to as the belly button, may also occur. The original umbilicus is attached, such as by sutures, into a new hole created by the surgeon.

A complete abdominoplasty is also referred to as a full abdominoplasty. In a complete abdominoplasty, an incision is made from hip to hip just above the pubic area. Another incision is made to separate the navel from the surrounding skin. The skin is detached from the abdominal wall to reveal the muscles and fascia to be tightened. The muscle fascia wall is tightened with sutures. The remaining skin and fat are tightened by removing the excess and closing. The old belly button stalk is brought out through a new hole and sutured into place. Liposuction may also be used to refine the transition zones of the abdominal contouring. A surgical dressing and optionally a compression garment are applied. Excess fluid from the site is drained. A complete abdominoplasty may also comprise a musculofascial plication abdominal dermal lipectomy and/or suction-assisted lipectomy of hips.

A partial abdominoplasty is also referred to as a mini abdominoplasty. In a partial abdominoplasty, a smaller incision is made as compared to a complete abdominoplasty. The skin and fat of the lower abdomen are detached in a more limited manner from the muscle fascia. The skin is stretched down and excess skin removed. The belly button stalk may be divided from the muscle below and the belly button slid down lower on the abdominal wall.

A portion of the abdominal muscle fascia wall is optionally tightened. Liposuction is often used to contour or sculpt the transition zone. The flap is stitched back into place. A combination abdominoplasty and liposuction procedure is often referred to as a "lipo-tuck". During such procedure, skin is removed and subsequently sutured. As noted above, the belly button is reattached to a new hole created by the surgeon.

An extended abdominoplasty is a complete abdominoplasty plus a lateral thigh lift. The patient is cut from the posterior axillary line. The operation includes all of the abdominal contouring of a complete abdominoplasty plus allows further improvement of the flank (waist), as well as smoothing the contour of the upper lateral thigh.

A high lateral tension tummy tuck is a more involved procedure and typically takes at least four and half hours to perform. In this method, in addition to vertical-line tightening as is the case in most conventional abdominoplasty procedures, muscles are also tightened horizontally. The procedure provides a patient with a flat abdomen and with an improved waistline.

A circumferential abdominoplasty, also referred to as a belt lipectomy or body lift, is an extended abdominoplasty in conjunction with a buttock lift. The incision typically runs all the way around the body. This surgical procedure is suitable, for example, for patients who have undergone massive weight loss.

The above procedures can be used alone or in combination. For example, an abdominoplasty may be conducted in the course of a lower body lift. Alternatively, abdominoplasty is combinable with liposuction contouring, breast reduction, breast lift, or a hysterectomy. Breast enhancement procedures performed in conjunction with an abdominoplasty are often referred to as a "mommy makeover". In such a procedure, barbed sutures may be employed.

An abdominoplasty procedure can be conducted using the device The typical fascial is done first, using a row of figure of eight sutures, first and then another layer of running suture all #1 PDS (polydioxanone suture, Ethicon) Two pieces of the device can be used as an onlay to augment the fascia tightening. One 10×25 cm piece can be used in the lower abdomen. It can be laced transversely, the vertical dimension 10 cm, can be positioned with the lower edge at level of the pubic symphsis, and the upper edge at the lower border of the umbilicus. The 25 cm transverse dimension can be suitable. A second scaffold can be cut and tailored to use in the supra-umbilcal region, with care taken not to leave too close to the umbilical closure. As the closure around the umbilicus occasionally may not heal primarily, extra care is taken with sutures/device in this location.

The handling characteristics can be excellent. The device is secured at its periphery with a 3-0 V-Lock (COVIDIEN brand of barbed suture, made of a material similar to PDS).

The patient can do very well and can be hospitalized overnight. The patient has a total of 5, ten mm flat blake drains—two that drain the back and three in the front. The patient stays on antibiotics until drains were which is typically within 10 to 20 days.

To summarize a device according to the present invention is a biocompatible, bioresorbable, pliable surgical matrix (mesh or scaffold) made preferably from the silk of the *Bombyx mori* silkworm. Because raw silk fibers are comprised of a fibroin protein core filament that is naturally coated with the antigenic globular protein sericin the sericin is removed by aqueous extraction. Yarn is then made from the sericin-depleted fibroin protein filaments by helical twisting to form a multi-filament protein fiber. The multi-filament protein fiber yarn is then knit into a three dimensional patterned matrix (mesh or scaffold) that can be used for soft tissue support and repair. The device upon implantation provides immediate physical and mechanical stabilization of tissue defects because of its strength and porous construction. Additionally, the porous lattice design of the device facilitate native tissue generation (that is tissue ingrowth) and neovascularization. The natural tissue repair process begins with deposition of a collagen network. This network integrates within the protein matrix, interweaving with the porous construct. Neovascularization begins with endothelial cell migration and blood vessel formation in the developing functional tissue network. This new functional tissue network and its corresponding vascular bed ensure the structural integrity and strength of the tissue. In the beginning stages of the tissue ingrowth process, the device provides the majority of structural support. The device (made of silk) is gradually deconstructed (bioresorbed) into its amino acid building blocks. The slow progression of the natural biological process of bioresorption allows for the gradual transition of support from the protein matrix of the device to the healthy native tissue thereby achieving the desired surgical outcome.

What is claimed is:

1. A process for making a pliable, knitted silk mesh, the process comprising the steps of:
   knitting a first silk yarn in a first wale direction using the knit pattern 3/1-1/1-1/3-3/3;
   knitting a second silk yarn in a second wale direction using the knit pattern 1/1-1/3-3/3-3/1;
   knitting a third silk yarn in a first course direction using the knit pattern 3/3-3/3-5/5-5/5-3/3-3/3-5/5-5/5-1/1-1/1-5/5-5/5-3/3-3/3-5/5-5/5-3/3-3/3-7/7-7/7; and
   knitting a fourth silk yarn in a second course direction using the knit pattern 1/1-5/5-5/5-3/3-3/3-5/5-5/5-3/3-3/3-7/7-7/7-3/3-3/3-5/5-5/5-3/3-3/3-5/5-5/5-1/1,
   thereby obtaining the pliable knitted silk mesh.

2. The process of claim 1, wherein (a) the two movements in the wale direction occur on separate needle beds (a knitting machine having two needle beds); and (b) with alternate yarns such as they knit with the opposing needle bed to their location (the front set of yarn knit with the back needle bed and the back set of yarn knit with the front needle bed).

3. The process of claim 1 wherein the silk yarns are made of a nine filaments twisted, and sericin depleted silk fibers.

4. The process of claim 1 wherein the yarns are made with three ends of raw silk yarn twisted together having a finesse of Td 20/22 twisted together in the S direction (clockwise direction of twist) to form a ply with 20 tpi (twist per inch is the number of twist measured in an inch of yarn) and further combining 3 of the resulting ply with 10 tpi in the Z direction (counter clockwise direction of twist).

5. The process of claim 1, wherein the stitch density or pick count for silk mesh design is about 40 picks per centimeter including the total picks count for the technical front face and the technical back face of the mesh, or equivalently about 20 picks per cm considering only one face of the mesh.

6. A process for making a pliable knitted silk mesh, the process comprising the steps of:
   knitting a first silk yarn in a first wale direction using the pattern 3/1-1/1-1/3-3/3;
   knitting a second silk yarn in a second wale direction using the pattern 1/1-1/3-3/3-3/1,
   knitting a third silk yarn in a first course direction using the pattern 3/3-3/3-5/5-5/5-3/3-3/3-5/5-5/5-1/1-1/1-5/5-5/5-3/3-3/3-5/5-5/5-3/3-3/3-7/7-7/7; and knitting a fourth silk yarn in a second course direction using the pattern 1/1-5/5-5/5-3/3-3/3-5/5-5/5-3/3-3/3-7/7-7/7-3/3-3/3-5/5-5/5-3/3-3/3-5/5-5/5-1/1, wherein:
(e) the two movements in the wale direction occur on separate needle beds with alternate yarns and loops that occur on every course are staggered within repeat,
(f) the silk yarns are made of a nine filament, twisted, and sericin depleted silk fibers,
(g) the yarns are made with 3 ends of Td 20/22 raw silk twisted together in the S direction to form a ply with 20 tpi and further combining 3 of the resulting ply with 10 tpi in the Z direction, and
(h) the stitch density or pick count for silk mesh design is 40 picks per centimeter including the total picks count for the technical front face and the technical back face of the mesh, or equivalently 20 picks per cm considering only one face of the mesh, thereby obtaining the pliable knitted silk mesh.

7. A pliable knitted silk mesh made by:

knitting a first silk yarn in a first wale direction using the pattern 3/1-1/1-1/3-3/3;

knitting a second silk yarn in a second wale direction using the pattern 1/1-1/3-3/3-3/1;

knitting a third silk yarn in a first course direction using the pattern 3/3-3/3-5/5-5/5-3/3-3/3-5/5-5/5-1/1-1/1-5/5-5/5-3/3-3/3-5/5-5/5-3/3-3/3-7/7-7/7; and knitting a fourth silk yarn in a second course direction using the pattern 1/1-5/5-5/5-3/3-3/3-5/5-5/5-3/3-3/3-7/7-7/7-3/3-3/3-5/5-5/5-3/3-3/3-5/5-5/5-1/1.

8. The pliable knitted silk mesh of claim 7, wherein the two movements in the wale direction occur on separate needle beds with alternate yarns and loops that occur on every course are staggered within repeat.

9. The pliable knitted silk mesh of claim 7, wherein the silk yarns are made of a nine filament, twisted, and sericin depleted silk fibers.

10. The pliable knitted silk mesh of claim 7, wherein the yarns are made with 3 ends of Td 20/22 raw silk twisted together in the S direction to form a ply with 20 tpi and further combining 3 of the resulting ply with 10 tpi in the Z direction.

11. The pliable knitted silk mesh of claim 7, wherein the stitch density or pick count for silk mesh design is 40 picks per centimeter including the total picks count for the technical front face and the technical back face of the mesh, or equivalently 20 picks per cm considering only one face of the mesh.

12. A pliable knitted silk mesh made by:

knitting a first silk yarn in a first wale direction using the pattern 3/1-1/1-1/3-3/3;

knitting a second silk yarn in a second wale direction using the pattern 1/1-1/3-3/3-3/1;

knitting a third silk yarn in a first course direction using the pattern 3/3-3/3-5/5-5/5-3/3-3/3-5/5-5/5-1/1-1/1-5/5-5/5-3/3-3/3-5/5-5/5-3/3-3/3-7/7-7/7; and knitting a fourth silk yarn in a second course direction using the pattern 1/1-5/5-5/5-3/3-3/3-5/5-5/5-3/3-3/3-7/7-7/7-3/3-3/3-5/5-5/5-3/3-3/3-5/5-5/5-1/1; wherein:
(a) the two movements in the wale direction occur on separate needle beds with alternate yarns and loops that occur on every course are staggered within repeat;
(b) the silk yarns are made of a nine filament, twisted, and sericin depleted silk fibers;
(c) the yarns are made with 3 ends of Td 20/22 ra(g) w silk twisted together in the S direction to form a ply with 20 tpi and further combining 3 of the resulting ply with 10 tpi in the Z direction; and
(d) the stitch density or pick count for silk mesh design is 40 picks per centimeter including the total picks count for the technical front face and the technical back face of the mesh, or equivalently 20 picks per cm considering only one face of the mesh.

* * * * *

UNITED STATES PATENT AND TRADEMARK OFFICE
CERTIFICATE OF CORRECTION

PATENT NO. : 9,308,070 B2
APPLICATION NO. : 14/462473
DATED : April 12, 2016
INVENTOR(S) : Mortarino et al.

It is certified that error appears in the above-identified patent and that said Letters Patent is hereby corrected as shown below:

On the title page

Item (56), in column 2, under "Other Publications", line 2, delete "Calciumchloride/Ethanol" and insert -- Calcium chloride/Ethanol --, therefor.

On the Page 4, item (56), in column 2, under "Other Publications", line 47, delete "Opthamology" and insert -- Ophthalmology --, therefor.

On the Page 4, item (56), in column 2, under "Other Publications", line 48, delete "Opthamology." and insert -- Ophthalmology. --, therefor.

On the Page 4, item (56), in column 2, under "Other Publications", line 59, delete "Long-Tem," and insert -- Long-Term, --, therefor.

On the Page 5, item (56), in column 1, under "Other Publications", line 15, delete "Mod" and insert -- Mori --, therefor.

On the Page 5, item (56), in column 2, under "Other Publications", line 22, delete "Biomatenals," and insert -- Biomaterials, --, therefor.

On the Page 5, item (56), in column 2, under "Other Publications", line 28, delete "Hexafluoro-Iso-Propanol" and insert -- Hexafluoro-Iso-Propanol --, therefor.

On the Page 5, item (56), in column 2, under "Other Publications", line 32, delete "Mod" and insert -- Mori --, therefor.

In the specification

Column 2, line 5, delete "Nephilia" and insert -- Nephila --, therefor.

Column 2, line 9, delete "s" and insert -- is --, therefor.

Column 2, line 42, delete "pliable." and insert -- pliable --, therefor.

Column 5, line 39, delete "1,thereby" and insert -- 1, thereby --, therefor.

Column 5, line 62, delete "[21] Our" and insert -- Our --, therefor.

Signed and Sealed this
Fifth Day of July, 2016

Michelle K. Lee
*Director of the United States Patent and Trademark Office*

CERTIFICATE OF CORRECTION (continued)

Column 7, line 25, delete "electromicrograph" and insert -- electron micrograph --, therefor.

Column 7, line 39, delete "1)" and insert -- 1). --, therefor.

Column 7, line 40, delete "FIGS." and insert -- FIG. --, therefor.

Column 7, line 45, delete "pattern)" and insert -- pattern). --, therefor.

Column 9, line 11, delete "The" and insert -- the --, therefor.

Column 10, line 51, delete "30N/mm" and insert -- 30 N/mm --, therefor.

Column 10, line 52, delete "N.mm" and insert -- N/mm --, therefor.

Column 10, line 58, delete "Products)" and insert -- Products). --, therefor.

Column 12, line 57, delete "Jakkob" and insert -- Jakob --, therefor.

Column 12, line 59, delete "the" and insert -- Yhe --, therefor.

Column 12, line 60, delete "Machinary" and insert -- Machinery --, therefor.

Column 12, line 67, delete "Gomez;" and insert -- Comez; --, therefor.

Column 13, line 9, delete "Machinary;" and insert -- Machinery; --, therefor.

Column 14, line 41, delete "active\" and insert -- active --, therefor.

Column 14, line 53, delete "coatings" and insert -- coatings. --, therefor.

Column 15, line 14, delete "Gomez;" and insert -- Comez; --, therefor.

Column 15, lines 41-42, delete "therefore" and insert -- therefor --, therefor.

Column 15, line 51, delete "Gomez" and insert -- Comez --, therefor.

Column 15, line 63, delete ""I"" and insert -- "/" --, therefor.

Column 21, lines 45-46, delete "symphsis," and insert -- symphysis, --, therefor.

Column 21, line 48, delete "supra-umbilcal" and insert -- supra-umbilical --, therefor.